(12) United States Patent
Takada et al.

(10) Patent No.: US 9,647,214 B2
(45) Date of Patent: May 9, 2017

(54) ORGANIC ELECTROLUMINESCENT ELEMENT, COMPOUND FOR ORGANIC ELECTROLUMINESCENT ELEMENT, AND LIGHT-EMITTING DEVICE, DISPLAY DEVICE, AND ILLUMINATION DEVICE USING SAID ELEMENT

(75) Inventors: Saki Takada, Kanagawa (JP); Koji Takaku, Kanagawa (JP); Yasunori Yonekuta, Kanagawa (JP); Toshihiro Ise, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 561 days.

(21) Appl. No.: 14/238,360

(22) PCT Filed: Aug. 6, 2012

(86) PCT No.: PCT/JP2012/069949
§ 371 (c)(1),
(2), (4) Date: May 13, 2014

(87) PCT Pub. No.: WO2013/024731
PCT Pub. Date: Feb. 21, 2013

(65) Prior Publication Data
US 2014/0339519 A1 Nov. 20, 2014

(30) Foreign Application Priority Data

Aug. 18, 2011 (JP) ................... 2011-179174

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 471/06* | (2006.01) | |
| *C07C 13/62* | (2006.01) | |
| *H01L 51/52* | (2006.01) | |
| *H01L 51/50* | (2006.01) | |

(52) U.S. Cl.
CPC .......... *H01L 51/0056* (2013.01); *C07C 13/62* (2013.01); *C07D 471/06* (2013.01); *C09K 11/06* (2013.01); *H01L 51/0054* (2013.01); *H01L 51/0057* (2013.01); *H01L 51/0067* (2013.01); *H01L 51/0072* (2013.01); *H01L 51/5203* (2013.01); *C07C 2101/16* (2013.01); *C07C 2103/54* (2013.01); *C07C 2103/94* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *H01L 51/0052* (2013.01); *H01L 51/0059* (2013.01); *H01L 51/0081* (2013.01); *H01L 51/5012* (2013.01)

(58) Field of Classification Search
CPC ......... C07C 13/00; C07C 13/32; C07C 13/62; C07C 13/64; C07C 43/267; C07C 211/61; C07C 217/94; C07C 323/38; C07C 2101/00; C07C 2101/12; C07C 2101/16; C07C 2103/00; C07C 2103/54; C07C 2103/93; C07C 2103/94; H05B 33/14; C07D 471/00; C07D 471/02; C07D 471/06; C07D 471/16; C07D 487/00; C07D 487/02; C07D 487/06; C07D 493/00; C07D 493/02; C07D 493/06; C07D 491/00; C07D 491/02; C07D 491/06; C07D 495/00; C07D 495/02; C07D 495/06; C07D 497/00; C07D 497/02; C07D 497/06; C07D 401/00; C07D 401/02; C07D 401/06; C07D 235/18; C07D 235/20; C07D 209/56; C07D 519/00; C07D 307/93; C07D 221/18; C07D 209/80; C09K 11/06; C09K 2211/00; C09K 2211/10; C09K 2211/1003; C09K 2211/1011; C09K 2211/1018; C09K 2211/1029; C09K 2211/1033; C09K 2211/1037; C09K 2211/1044; C09K 2211/1088; C09K 2211/1092; C09K 2211/1096; H01L 51/0032; H01L 51/005; H01L 51/0051; H01L 51/0052; H01L 51/0054; H01L 51/0056; H01L 51/0057; H01L 51/0058; H01L 51/0059; H01L 51/006; H01L 51/0071; H01L 51/0072; H01L 51/0073; H01L 51/0074; H01L 51/0081;
(Continued)

(56) References Cited

U.S. PATENT DOCUMENTS

| 2008/0124455 | A1* | 5/2008 | Shin ...................... C07D 209/80 427/66 |
| 2011/0108821 | A1* | 5/2011 | Kaiser ..................... C07C 13/62 257/40 |

FOREIGN PATENT DOCUMENTS

| JP | 2006512395 | 4/2006 |
| JP | 2010111620 | 5/2010 |

(Continued)

*Primary Examiner* — Andrew K Bohaty
(74) *Attorney, Agent, or Firm* — Riverside Law LLP

(57) ABSTRACT

An organic electroluminescent element using a compound represented by the following general formula (I) emits dark blue light and has a high effect of inhibition of voltage during high-luminance driving:

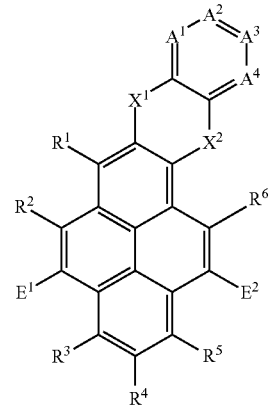

wherein $R^1$ to $R^6$; $E^1$ and $E^2$; $X^1$ and $X^2$; and $A^1$ to $A^8$ are as defined herein.

17 Claims, 2 Drawing Sheets

(58) Field of Classification Search
CPC ............. H01L 51/0061; H01L 51/0065; H01L 51/0068; H01L 51/0094; H01L 51/50; H01L 51/5012; H01L 51/5016; H01L 51/5024; H01L 51/5203

USPC ..... 428/690, 691, 917, 411.4, 336; 427/458, 427/66; 313/500–512; 257/40, 88–104, 257/E51.001–E51.052; 252/301.16–301.35; 546/14, 30, 31, 41; 548/406, 407, 417; 549/24, 41, 214, 381, 549/456; 556/406; 585/26, 27; 544/229, 544/245, 338

See application file for complete search history.

(56) References Cited

FOREIGN PATENT DOCUMENTS

| | | |
|---|---|---|
| JP | 201179822 | 4/2011 |
| KR | 10-20110006915 | 1/2011 |
| KR | 10-20120081539 | 7/2012 |
| WO | 2010012328 | 2/2010 |

\* cited by examiner (A) LUMO
φ:54/260 ε:-0.0544
homo:53 k:0.0300

(B) HOMO
φ:53/260 ε:-0.1957
homo:53 k:0.0300

ORGANIC ELECTROLUMINESCENT ELEMENT, COMPOUND FOR ORGANIC ELECTROLUMINESCENT ELEMENT, AND LIGHT-EMITTING DEVICE, DISPLAY DEVICE, AND ILLUMINATION DEVICE USING SAID ELEMENT

CROSS-REFERENCE TO RELATED APPLICATIONS

This application is a national stage entry of International Patent Application No. PCT/JP2012/069949, filed 6 Aug. 2012, which in turn claims priority to, and the benefit of, Japanese Patent Application No. 2011-179174, filed 18 Aug. 2011, all of which are incorporated herein by reference in their entireties.

TECHNICAL FIELD

The present invention relates to an organic electroluminescent element, and a material compound for an organic electroluminescent element used therefor. The present invention further relates to a light emitting device, a display device, or an illumination device, using the organic electroluminescent element.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have an organic layer between a pair of electrodes, and utilize, for light emitting, energy of the exciton generated as a result of recombination of the electron injected from the cathode and the hole injected from the anode in the organic layer. The organic electroluminescent elements can provide as an element having diverse light emitting wavelengths, and since they have a high response speed and are relatively thin and light-weight, it is expected that they can be employed in a wide range of applications. Above all, it is employed to develop the development of an organic electroluminescent element having high color purity and luminous efficiency is important in applications with full-color displays and the like, and the results of studies on various research and development have been reported.

PTL 1 describes that it is possible to attain light emission and a longer service life in the blue region of an element using a material in which a ring is formed with a single bond and a methylene chain with respect to a fused ring structure such as pyrene as a fluorescent material. In Examples of this literature, 3 kinds of compounds are used as a blue dopant which has a chromaticity of about (0.14 or 0.16) and a maximum efficiency of about 7.8 cd/A, described in Table 6.

Furthermore, the literature 2, which is well-known, describes that an element having high efficiency and a wide gap (that is, considered to allow blue light emission to be performed) is obtained by using a molecule formed by subjecting benzofluorene to ring fusion and expansion as a light emitting material. In Examples of this literature, the spectrum of the element thus fabricated is disclosed, in which the wavelength is in a long and broad wave form and the maximum light emitting wavelength was about 462 nm on average.

CITATION LIST

Patent Literature

PTL 1: WO2010/012328
PTL 2: JP-T-2006-512395

SUMMARY OF INVENTION

Technical Problem

However, the present inventors have investigated, and as a result, they have found that the chromaticity of the organic electroluminescent elements described in PTLs 1 and 2 above may still be insufficient for dark blue colors in display applications or the like, and there is a further need for achieving darker blue light emission. In addition, they have further found that such organic electroluminescent elements have a low effect of inhibition of voltage during high-luminance driving.

The present invention aims to solve the foregoing problems. That is, it is an object of the present invention to provide an organic electroluminescent element which emits dark blue light and has a high effect of inhibition of voltage during high-luminance driving.

Solution to Problem

Therefore, the present inventors have conducted extensive investigations for the purpose of providing an organic electroluminescent element which emits dark blue light and has a high effect of inhibition of voltage during high-luminance driving.

Here, PTL 1 mentions a position of a pyrene skeleton to which non-aromatic rings are fused and the rings are preferably fused in the major axis direction of the pyrene, but does not specifically describe the reason or the detailed mechanism thereof. On the other hand, PTL 2 does not describe a good position to which a pyrene skeleton has ring fusion, as seen from the use of the exemplary compound used in [0119], having a structure having non-aromatic rings fused so as to connect the major axis direction and the minor axis direction of two molecules of pyrene.

In such a circumstance, the inventors have determined a calculated structure of the highest occupied molecular orbital (HOMO) and the lowest unoccupied molecular orbital (LUMO) of pyrene for the unsubstituted pyrene molecule. The results are shown in FIG. 4 below. From FIG. 4, it can be seen that there is no difference between the major axis direction and the minor axis direction of pyrene, from which it could not be assumed that the electronic properties are changed by changing a ring fusion position of the pyrene skeleton in that situation.

Accordingly, it could not be expected at all whether a material for an organic electroluminescent element, which emits dark blue light and has a high effect of inhibition of voltage during high-luminance driving by changing the structure of the pyrene-based compound, can be obtained or not, from the knowledge or calculation theory in the related art in that situation.

In this regard, the present inventors have found that by using a pyrene-based compound in a specific structure having a ring fused in a specific direction as a light emitting dopant for an element, an organic electroluminescent element which emits dark blue light and has a high effect of inhibition of voltage during high-luminance driving can be obtained, which could not have been achieved in the related art. They have further found that the skeleton of such a compound having the structure itself emits short-wavelength light and it is not necessary to shorten the wavelength by additionally introducing a substituent having a specific structure into the skeleton as in the fluorescent light emitting materials known in the related art.

That is, the present inventors have found that by using a pyrene derivative having a specific structure, the aforementioned problems can be solved, thereby completing the present invention as described below.

[1] An organic electroluminescent element having:

a substrate, a pair of electrodes including an anode and a cathode, disposed on the substrate, and at least one organic layer including a light emitting layer, disposed between the electrodes, in which at least one kind of compound represented by the following general formula (I) is contained in any layer of the at least one organic layer.

[Chem. 1]

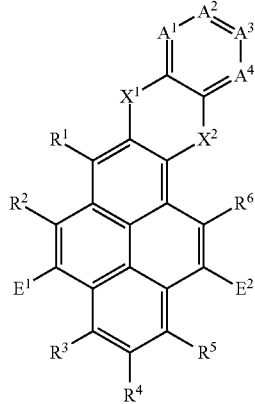

General formula (I)

[In the general formula (I), $R^1$ to $R^6$ each independently represent a hydrogen atom or a substituent, but there is no case where two adjacent groups out of $R^1$ to $R^6$ are bonded to each other to form a ring. $E^1$ and $E^2$ each independently represent a hydrogen atom or a substituent. The members of only one set of $E^1$ and $R^2$, $E^1$ and $R^3$, $E^2$ and $R^6$, and $E^2$ and $R^5$ are bonded to each other to form a structure represented by the following general formula (E-1), and the members of the other sets are not bonded to each other to form a ring.

[Chem. 2]

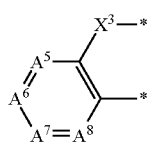

General formula (E-1)

* represents a position for bonding to the pyrene skeleton. Among $X^1$ and $X^2$, one represents a single bond and the other represents any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent. $A^1$ to $A^8$ each independently represent $CR^{116}$ or N. $R^{116}$ represents a hydrogen atom or a substituent, and when two adjacent groups out of $A^1$ to $A^4$ are $CR^{116}$, the two $R^{116}$'s may be bonded to each other to form a ring structure.]

[2] The organic electroluminescent element as described in [1], in which the compound represented by the general formula (I) is a compound represented by the following general formula (II).

[Chem. 3]

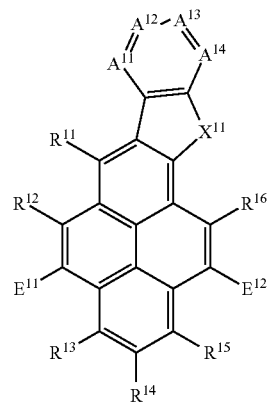

General formula (II)

[In the general formula (II), $R^{11}$ to $R^{16}$ each independently represent a hydrogen atom or a substituent, but there is no case where two adjacent groups out of $R^{11}$ to $R^{16}$ are bonded to each other to form a ring. $E^{11}$ and $E^{12}$ each independently represent a hydrogen atom or a substituent. The members of only one set of $E^{11}$ and $R^{12}$, $E^{11}$ and $R^{13}$, $E^{12}$ and $R^{16}$, and $E^{12}$ and $R^{15}$ are bonded to each other to form a structure represented by the following general formula (E-1), and the members of the other sets are not bonded to each other to form a ring.

[Chem. 4]

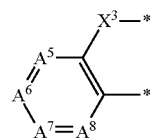

General formula (E-1)

* represents a position for bonding to the pyrene skeleton. $X^{11}$ and $X^2$ each independently represent any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent. $A^{11}$ to $A^{14}$ and $A^5$ to $A^8$ each independently represent $CR^{116}$ or N. $R^{116}$ represents a hydrogen atom or a substituent, and when two adjacent groups out of $A^{11}$ to $A^{14}$ and $A^5$ to $A^8$ are $CR^{116}$, the two $R^{116}$'s may be bonded to each other to form a ring structure.]

[3] The organic electroluminescent element as described in [1], in which the compound represented by the general formula (I) is a compound represented by the following general formula (III).

[Chem. 5]

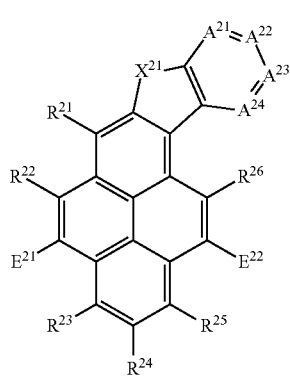

General formula (III)

[Chem. 7]

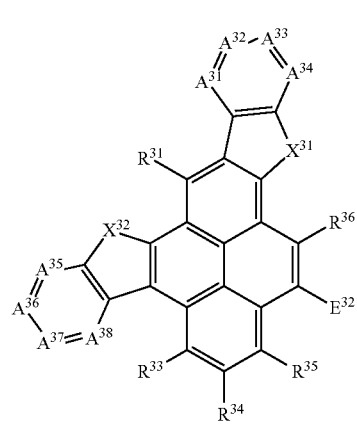

General formula (IV)

[In the general formula (III), $R^{21}$ to $R^{26}$ each independently represent a hydrogen atom or a substituent, but there is no case where two adjacent groups out of $R^{21}$ to $R^{26}$ are bonded to each other to form a ring. $E^{21}$ and $E^{22}$ each independently represent a hydrogen atom or a substituent. The members of only one set of $E^{21}$ and $R^{22}$, $E^{21}$ and $R^{23}$, $E^{22}$ and $R^{26}$, and $E^{22}$ and $R^{25}$ are bonded to each other to form a structure represented by the following general formula (E-1) and the members of the other sets are not bonded to each other to form a ring.

[Chem. 6]

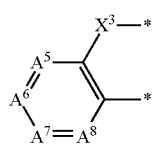

General formula (E-1)

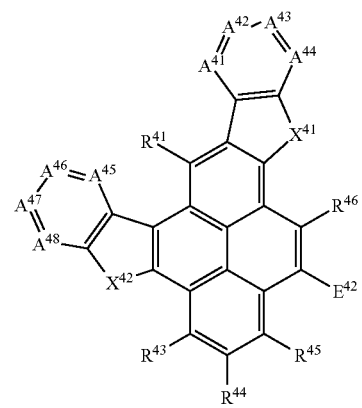

General formula (V)

* represents a position for bonding to the pyrene skeleton. $X^{21}$ and $X^2$ each independently represent any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent. $A^{21}$ to $A^{24}$ and $A^5$ to $A^8$ each independently represent $CR^{116}$ or N. $R^{116}$ represents a hydrogen atom or a substituent, and when two adjacent groups out of $A^{21}$ to $A^{24}$ and $A^5$ to $A^8$ are $CR^{116}$, the two $R^{116}$'s may be bonded to each other to form a ring structure.]

The organic electroluminescent element as described in [2], in which the compound represented by the general formula (II) is a compound represented by any one of the following general formulae (IV) to (VII).

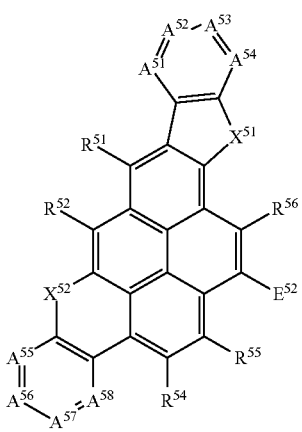

General formula (VI)

General formula (VII)

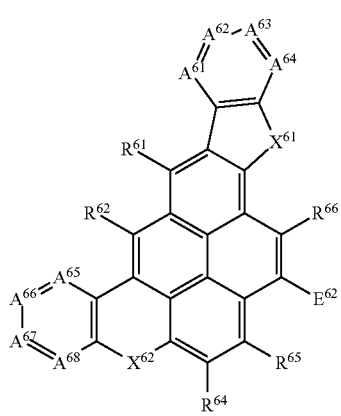

[In the general formulae (IV) to (VII), $R^{31}$ to $R^{66}$ and $E^{32}$ to $E^{62}$ each independently represent a hydrogen atom or a substituent, but there is no case where two adjacent groups out of $R^{31}$ to $R^{66}$ and $E^{32}$ to $E^{62}$ are bonded to each other to form a ring. $X^{32}$ to $X^{62}$ represent any linking group of $CR^{111}R^{112}$, $NR^{113}$, O, S, and $SiR^{114}R^{115}$. $R^{111}$ to $R^{115}$ each independently represent a hydrogen atom or a substituent.

$A^{31}$ to $A^{68}$ each independently represent $CR^{116}$ or N. $R^{116}$ represents a hydrogen atom or a substituent, and when two adjacent groups out of $A^{31}$ to $A^{68}$ are $CR^{116}$, the two $R^{116}$'s may be bonded to each other to form a ring structure.]

[5] The organic electroluminescent element as described in [2], in which the compound represented by the general formula (II) is a compound represented by any one of the following general formulae (VIII) to (XI).

[Chem. 8]

General formula (VIII)

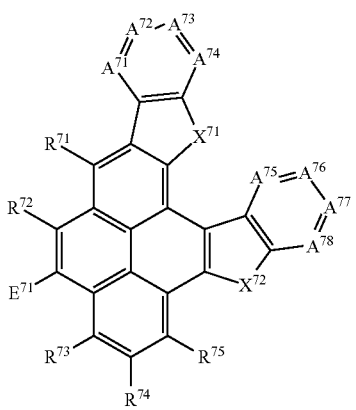

General formula (IX)

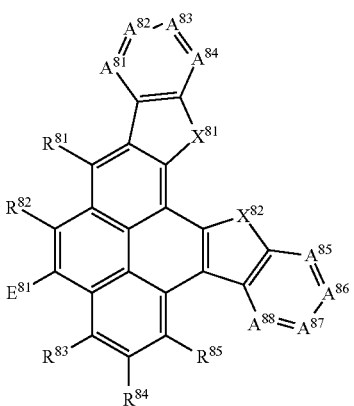

General formula (X)

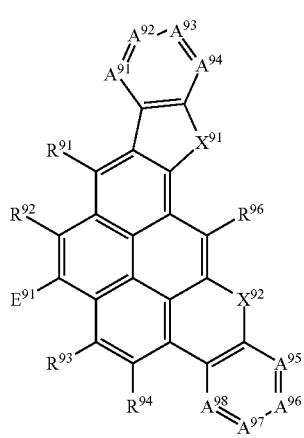

General formula (XI)

[In the general formulae (VIII) to (XI), $R^{71}$ to $R^{106}$ and $E^{72}$ to $E^{102}$ each independently represent a hydrogen atom or a substituent, but there is no case where two adjacent groups out of $R^{71}$ to $R^{106}$ and $E^{72}$ to $E^{102}$ are bonded to each other to form a ring. $X^{72}$ to $X^{102}$ represent any linking group of $CR^{111}R^{112}$, $NR^{113}$, O, S, and $SiR^{114}R^{115}$. $R^{111}$ to $R^{115}$ each independently represent a hydrogen atom or a substituent. $A^{71}$ to $A^{108}$ each independently represent $CR^{116}$ or N. $R^{116}$ represents a hydrogen atom or a substituent, and when two adjacent groups out of $A^{71}$ to $A^{108}$ are $CR^{116}$, the two $R^{116}$'s may be bonded to each other to form a ring structure.]

[6] The organic electroluminescent element as described in any one of [1] to [5], in which the molecular weight of the compound represented by the general formula (I) is 800 or less.

[7] The organic electroluminescent element as described in any one of [1] to [6], in which the compound represented by the general formula (I) is contained in the light emitting layer.

[8] The organic electroluminescent element as described in [7], in which the compound represented by the general formula (I) is a light emitting material contained in the light emitting layer.

[9] The organic electroluminescent element as described in [8], further including a host material in the light emitting layer.

[10] The organic electroluminescent element as described in [9], in which the host material has a hydrocarbon fused ring structure having 10 to 50 carbon atoms.

[11] The organic electroluminescent element as described in [9], in which the host material has an anthracene skeleton.

[12] The organic electroluminescent element as described in any one of [1] to [11], in which the organic layer containing the compound represented by the general formula (I) is formed by a vacuum deposition process.

[13] The organic electroluminescent element as described in any one of [1] to [11], in which the light emitting layer is formed by a wet process.

[14] A light emitting device using the organic electroluminescent element as described in any one of [1] to [13].

[15] A display device using the organic electroluminescent element as described in any one of [1] to [13].

[16] An illumination device using the organic electroluminescent element as described in any one of [1] to [13].

[17] A compound represented by the following general formula (I).

[Chem. 9]

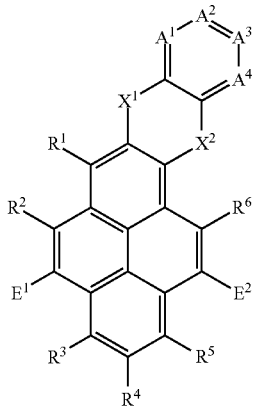

General formula (I)

[In the general formula (I), $R^1$ to $R^6$ each independently represent a hydrogen atom or a substituent, but there is no case where two adjacent groups out of $R^1$ to $R^6$ are bonded to each other to form a ring. $E^1$ and $E^2$ each independently represent a hydrogen atom or a substituent. The members of only one set of $E^1$ and $R^2$, $E^1$ and $R^3$, $E^2$ and $R^6$, and $E^2$ and $R^5$ are bonded to each other to form a structure represented by the following general formula (E-1), and the members of the other sets are not bonded to each other to form a ring.

[Chem. 10]

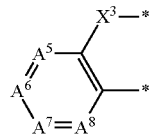

General formula (E-1)

* represents a position for bonding to the pyrene skeleton. Among $X^1$ and $X^2$, one represents a single bond and the other represents any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent.

$A^1$ to $A^8$ each independently represent $CR^{116}$ or N. $R^{116}$ represents a hydrogen atom or a substituent, and when two adjacent groups out of $A^1$ to $A^4$ are $CR^{116}$, the two $R^{116}$'s may be bonded to each other to form a ring structure.]

Advantageous Effects of Invention

The organic electroluminescent element of the present invention has advantageous effects of emitting dark blue light and having a high inhibition of voltage effect during high-luminance driving. Further, if the material for an organic electroluminescent element of the present invention is used, such an excellent organic electroluminescent element can be easily prepared. In addition, the light emitting device, the display device, and the illumination device of the present invention have advantageous effects of having low power consumption, excellent chromaticity, and a small change in the chromaticity during luminance modulation even when used in a device requiring luminance modulation, and are suitable particularly in display applications requiring light emission at various levels of luminance.

DESCRIPTION OF EMBODIMENTS

Figure 1:
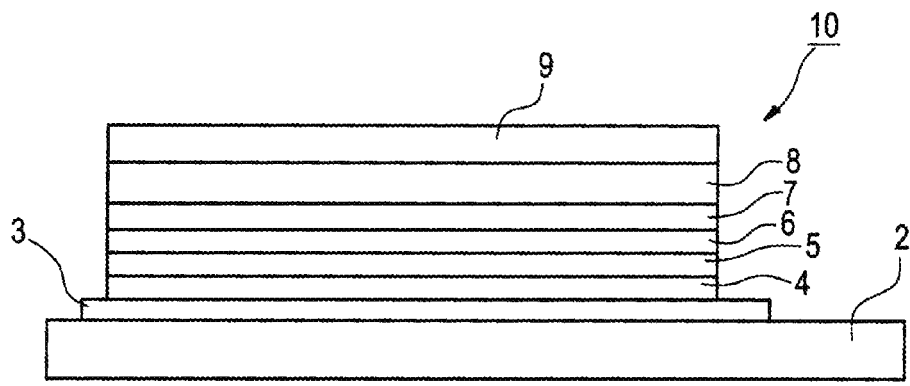
FIG. 1 is a schematic view showing one example of a configuration of an organic electroluminescent element according to the present invention.

Hereinafter, the details of the present invention will be described. The description of the requirements of the configuration as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Light Emitting Material for Organic Electroluminescent Element, Represented by General Formula (I)]

The organic electroluminescent element of the present invention has at least a substrate, a pair of electrodes including an anode and a cathode, disposed on the substrate, and at least one organic layer including a light emitting layer, disposed between the electrodes. The organic electroluminescent element of the present invention contains at least one kind of compound represented by the following general formula (I) on several organic layers.

[Chem. 11]

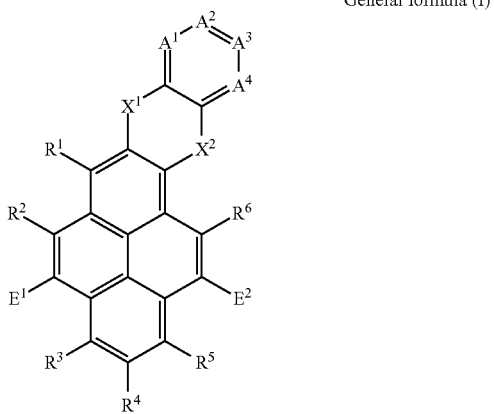

General formula (I)

In the general formula (I), $R^1$ to $R^6$ each independently represent a hydrogen atom or a substituent, but there is no case where two adjacent groups out of $R^1$ to $R^6$ are bonded to each other to form a ring. $E^1$ and $E^2$ each independently represent a hydrogen atom or a substituent. The members of only one set of $E^1$ and $R^2$, $E^1$ and $R^3$, $E^2$ and $R^6$, and $E^2$ and $R^5$ are bonded to each other to form a structure represented by the following general formula (E-1) and the members of the other sets are not bonded to each other to form a ring.

[Chem. 12]

General formula (E-1)

* represents a position for bonding to the pyrene skeleton. For $X^1$ and $X^2$, one represents a single bond and the other represents any linking group of any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent. $A^1$ to $A^8$ each independently represent $CR^{116}$ or N. $R^{116}$ represents a hydrogen atom or a substituent, and when two adjacent groups out of $A^1$ to $A^4$ are $CR^{116}$, the two $R^{116}$'s may be bonded to each other to form a ring structure.

The present inventors have found that it is possible to attain sufficient dark blue light emission and inhibition of voltage during high-luminance driving by using pyrene with a fused ring, in which an aromatic ring is in contact at a position as shown by the general formula (I). This is presumed to be due to an action that a dipole moment is not mutually canceled by winding the ring asymmetrically with respect to the pyrene center and the molecules are prevented from accessing to each other in the same direction as in the general formula (I).

For polycyclic compounds in the related art, which do not have a characteristic structure as represented by the general formula (I), it is necessary to introduce a polar group as a substituent in order to achieve sufficient dark blue light emission. However, when such a polar group is introduced, there occur problems, for example, that the durability of the compound is reduced or a too high dipole moment leads to promotion of a longer wavelength, inmost cases. In this regard, since the compound represented by the general formula (I) has such a structure that the molecules are less accessible to each other and has a structure having a fused ring in two different directions with respect to the pyrene, local molecular orientation in the film is reduced, and thus, the charge mobility in the planar direction is uniform. Therefore, it is thought that the sufficient dark blue light emission can be achieved, and high inhibition of voltage during high-luminance driving, for which requires for a number of charges to be transported, can also be achieved.

That is, the light emitting material for an organic electroluminescent element, represented by the general formula (I), contributes to shortening of the wavelength and inhibition of voltage during high-luminance in its mother skeleton. In this regard, the light emitting material represented by the general formula (I) is not limited in the substituent of the mother skeleton and the effects above can be obtained. However, in a preferred aspect of the present invention, shortening of the wavelength and inhibition of voltage during high-luminance driving may be carried out with the use of a specific substituent.

Hereinbelow, the light emitting material represented by the general formula (I) will be described in detail.

In the general formula (I), for $X^1$ and $X^2$, one represents a single bond and the other represents any linking group of any linking group of $CR^{111}R^{112}$, $NR^{113}$, O, S, and $SiR^{114}R^{115}$. It is preferable that any one of $X^1$ and $X^2$ be $CR^{111}R^{112}$ or $NR^{113}$, from the viewpoint of preferred luminous color.

In the general formula (I), $A^1$ to $A^4$ each independently represent $CR^{116}$ or N. In $A^1$ to $A^4$, the number of N's is preferably 0 to 2, more preferably 0 or 1, and particularly preferably 0. That is, a case where $A^1$ to $A^4$ are both $CR^{116}$ can be mentioned as a preferred example. Further, when the number of N's is 1, for example, a case where $A^4$ is N can be mentioned as a preferred example.

In $CR^{116}$, the carbon atom is a ring-constituting atom of the light emitting material represented by the general formula (I), and $R^{116}$ represents a hydrogen atom or a substituent, which is bonded to the carbon atom. Further, as used in the present specification, the substituent includes those in which the substituent is further substituted with a substituent. $R^{116}$ is a hydrogen atom or a substituent, and specific examples of the substituent include the following Substituent Group A. When $R^{116}$ is a substituent, the substituent is preferably an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing any one of N, O, and S as a hetero atom), or a di-substituted amino group (more preferably a dialkylamino group or a diarylamino group; the preferred ranges of the alkyl group and the aryl group in this case are the same as the preferred ranges of the alkyl group and the aryl group in $R^1$), a halogeno group (preferably having a fluoro group), a cyano group, or a nitro group. Further, $R^{116}$'s bonded to the adjacent carbon atom may be bonded to each other to form a cyclic structure. Examples of such a cyclic structure include an aryl group (more preferably an aryl group having 6 to 14 carbon atoms), and a heteroaryl group (preferably a heteroaryl group having 5 to 20 carbon atoms and containing any one of N, O, and S as a hetero atom), and more preferably an aryl group. When two adjacent groups out of $A^1$ to $A^4$ are $CR^{116}$, the two $R^{116}$'s may be bonded to each other to form a ring structure. The ring structure thus formed may be any one of an aromatic ring, a heterocycle, and a non-aromatic ring. When $R^{116}$ is a substituent, it is preferable that the substituent be a di-substituted amino group or $R^{116}$'s bonded to the adjacent carbon atom be bonded to each other to form a cyclic structure.

$R^{111}$ to $R^{116}$ each independently represent a hydrogen atom or a substituent. Examples of $R^{111}$, $R^{112}$, $R^{114}$ and $R^{115}$ include the following Substituent Group A, and examples of $R^{113}$ include the following Substituent Group B.

<<Substituent Group A (Group of Substituents at Carbon Atom and Substituents at Silicon Atom)>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, anthranyl), amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxy group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

<<Substituent Group B (Group of Substituents at Nitrogen Atom)>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group). These substituents may be further substituted, and examples of the additional substituent include the groups selected from the Substituent Group B as described above. Further, the substituent substituted with a substituent may be further substituted, and examples of the additional substituent include the groups selected from the Substituent Group B as described above. In addition, the substituent substituted with the substituent substituted with a substituent may be further substituted, and examples of the additional substituent include the groups selected from the Substituent Group B as described above.

$R^{111}$, $R^{112}$, $R^{114}$ to $R^{116}$ preferably each independently represent an alkyl group (more preferably a linear, branched, or cyclic alkyl group having 1 to 10 carbon atoms), an aryl group (more preferably an aryl group having 6 to 14 carbon atoms), or a heteroaryl group (preferably a heteroaryl group having 5 to 20 carbon atoms and containing at least any one of N, O, and S as a hetero atom), and more preferably a linear or branched alkyl group having 1 to 6 carbon atoms or an aryl group having 6 to 10 carbon atoms. In addition, it is preferable that $R^{111}$ and $R^{112}$ be the same as each other and $R^{114}$ and $R^{115}$ be also the same as each other, from the viewpoint of easiness of synthesis. In addition, such a substituent may be further substituted with one or more substituents.

$R^{113}$ is more preferably any one of a linear, branched, or cyclic alkyl group having 1 to 10 carbon atoms, an aryl group having 6 to 50 carbon atoms, and a heteroaryl group having 5 to 20 carbon atoms and containing at least any one of N, O, and S as a hetero atom, and still more preferably any one of an aryl group having 6 to 14 carbon atoms and a heteroaryl group having 5 to 20 carbon atoms and containing at least any one of N, O, and S as a hetero atom.

For $X^1$ and $X^2$ in the general formula (I), one represents a single bond and the other represents any linking group of $CR^{111}R^{112}$, $NR^{113}$, O, S, and $SiR^{114}R^{115}$. As used herein, the definitions and the preferred ranges of $R^{111}$ to $R^{115}$ are the same as the definitions and the preferred ranges of $R^{111}$ to $R^{115}$.

In the general formula (I), $R^1$ to $R^8$ each independently represent a hydrogen atom or a substituent. As mentioned herein, examples of the substituent include the Substituent Group A as described above. $R^1$ to $R^8$ preferably represent an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing at least any one of N, O, and S as a hetero atom), a di-substituted amino group (more preferably a dialkylamino group or a diarylamino group; the preferred range of the alkyl or aryl in this case is the same as the alkyl or aryl in $R^1$ to $R^8$), a halogeno group (preferably a fluoro group), a cyano group, or a nitro group. Further, such a substituent may be substituted with any one or more substituents, and the preferred range of the substituent in this case is the same as the substituent in $R^1$ to $R^8$.

In the general formula (I), $R^1$ to $R^6$ each independently represent a hydrogen atom or a substituent, but there is no case where two adjacent groups out of $R^1$ to $R^6$ are bonded to each other to form a ring. $R^1$ to $R^6$ are preferably an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing at least any one of N, O, and S as a hetero atom), a di-substituted amino group (more preferably a dialkylamino group or a diarylamino group; the preferred range of the alkyl or aryl in this case is the same as the alkyl or aryl in $R^1$ to $R^6$), a halogeno group (preferably a fluoro group), a cyano group, or a nitro group, and still more preferably an alkyl group having 1 to 6 carbon atoms or an aryl group having 6 to 10 carbon atoms. In addition, $R^1$ to $R^6$ may be substituted with any one or more substituents, and the preferred range of the substituent in this case is the same as in $R^2$ to $R^6$.

One or more of $R^1$ to $R^6$ are preferably a substituent represented by any one of the following general formulae.

[Chem. 13]

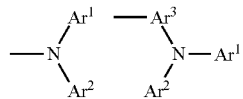

$Ar^1$ and $Ar^2$ each independently represent an aryl group, $Ar^3$ represents a divalent arylene group. $Ar^1$ and $Ar^2$ are preferably a substituted or unsubstituted phenyl or naphthyl, and more preferably a substituted or unsubstituted phenyl.

Ar$^3$ is preferably a substituted or unsubstituted phenylene or naphthylene, more preferably a substituted or unsubstituted phenylene, and most preferably a substituted or unsubstituted p-phenylene.

In the present invention, R$^1$ to R$^6$ may be all hydrogen atoms. 0 to 4 groups out of R$^1$ to R$^6$ are preferably substituents, 0 to 2 groups are more preferably substituents, and 0 or 1 group are still more preferably a substituent.

In the general formula (I), there is no case where R$^1$ to R$^6$ bonded to the adjacent ring skeleton atom are bonded to each other to form a ring. As used herein, the "ring" includes both of a case where an aromatic ring or a heterocycle is newly fused and a case where a non-aromatic ring is formed. As used herein, specific examples of the non-aromatic ring include the following structures.

[Chem. 14]

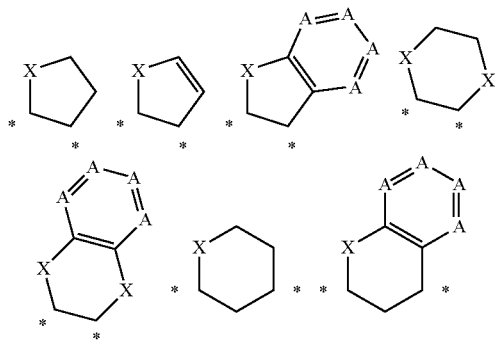

In the formulae above, X's each independently represent a hetero atom, and examples of the hetero atom include a nitrogen atom, an oxygen atom, and a sulfur atom. A's each independently represent CR$^{111}$R$^{112}$ or NR$^{113}$, and the definitions of R$^{111}$ to R$^{113}$ are as described above.

E$^1$ and E$^2$ each independently represent a hydrogen atom or a substituent. The members of only one set of E$^1$ and R$^2$, E$^1$ and R$^3$, E$^2$ and R$^6$, and E$^2$ and R$^5$ are bonded to each other to form a structure represented by the following general formula (E-1) and the members of the other sets are not bonded to each other to form a ring.

[Chem. 15]

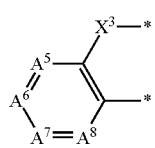

General formula (E-1)

* represents a position for bonding to the pyrene skeleton. For example, when E$^1$ and R$^2$ are bonded to each other to form a structure represented by the general formula (E-1), any one of E$^1$ and R$^2$ may be on the side X$^2$ in the general formula (E-1). This also applies to the sets other than the set of E$^1$ and R$^2$. The definitions and the preferred ranges of A$^5$ to A$^8$ are the same as the definitions and the preferred ranges of A$^1$ to A$^4$ above. X$^3$ represents any linking group of CR$^{111}$R$^{112}$, NR$^{113}$, O, S, and SiR$^{114}$R$^{115}$. The definitions and the preferred ranges of R$^{111}$ to R$^{115}$ are the same as above.

The light emitting material represented by the general formula (I) is preferably a compound represented by the following general formula (II).

[Chem. 16]

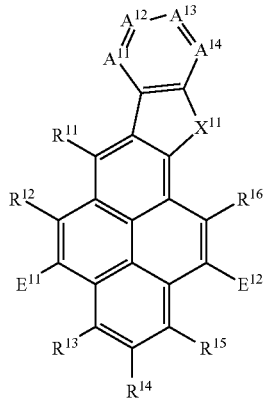

General formula (II)

In the general formula (II), R$^{11}$ to R$^{16}$ each independently represent a hydrogen atom or a substituent, but there is no case where two adjacent groups out of R$^{11}$ to R$^{16}$ are bonded to each other to form a ring. E$^{11}$ and E$^{12}$ each independently represent a hydrogen atom or a substituent. The members of only one set of E$^{11}$ and R$^{12}$, E$^{11}$ and R$^{13}$, E$^{12}$ and R$^{16}$, and E$^{12}$ and R$^{15}$ are bonded to each other to form a structure represented by the following general formula (E-1) and the members of the other sets are not bonded to each other to form a ring.

[Chem. 17]

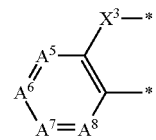

General formula (E-1)

* represents a position for bonding to the pyrene skeleton. X$^3$ represents any linking group of CR$^{111}$R$^{112}$, NR$^{113}$, O, S, and SiR$^{114}$R$^{115}$. R$^{111}$ to R$^{115}$ each independently represent a hydrogen atom or a substituent. A$^{11}$ to A$^{14}$ and A$^5$ to A$^8$ each independently represent CR$^{116}$ or N. R$^{116}$ represents a hydrogen atom or a substituent, and when two adjacent groups out of A$^{11}$ to A$^{14}$ and A$^5$ to A$^8$ are CR$^{116}$, the two R$^{116}$'s may be bonded to each other to form a ring structure.

The preferred ranges of R$^{11}$ to R$^{16}$, E$^{11}$, E$^{12}$, X$^3$, R$^{111}$ to R$^{115}$, A$^{15}$ to A$^{14}$, A$^5$ to A$^8$ in the general formula (II) are the same as the preferred ranges of R$^1$ to R$^6$, E$^1$, E$^2$, X$^3$, R$^{111}$ to R$^{115}$, A$^1$ to A$^4$, A$^5$ to A$^8$ in the general formula (I).

The compound represented by the general formula (II) is represented by any one of the following general formulae (IV) to (VII) when E$^1$ represents the general formula (E-1).

[Chem. 18]

General formula (IV)

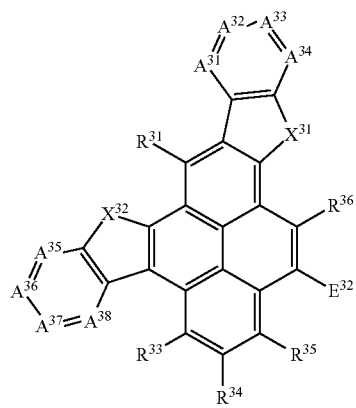

General formula (V)

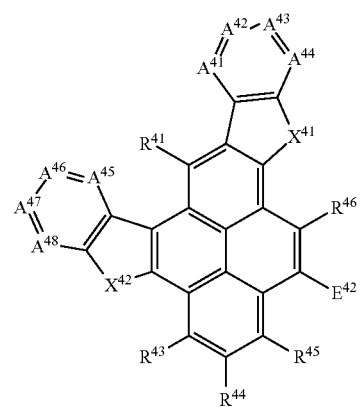

General formula (VI)

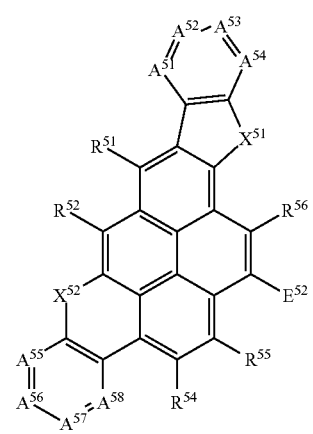

General formula (VII)

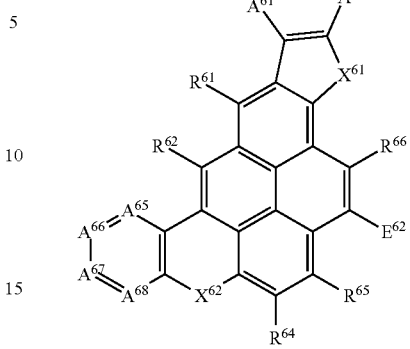

In the general formulae (IV) to (VII), $R^{31}$ to $R^{66}$ and $E^{32}$ to $E^{62}$ each independently represent a hydrogen atom or a substituent, but there is no case where two adjacent groups out of $R^{31}$ to $R^{66}$ and $E^{32}$ to $E^{62}$ are bonded to each other to form a ring. $X^{32}$ to $X^{62}$ represent any linking group of $CR^{111}R^{112}$, $NR^{113}$, O, S, and $SiR^{114}R^{115}$. $R^{111}$ to $R^{115}$ each independently represent a hydrogen atom or a substituent. $A^{31}$ to $A^{68}$ each independently represent $CR^{116}$ or N. $R^{116}$ represents a hydrogen atom or a substituent, and when two adjacent groups out of $A^{31}$ to $A^{68}$ are $CR^{116}$, the two $R^{116}$'s may be bonded to each other to form a ring structure.

When $E^2$ represents the general formula (E-1), the compound represented by the general formula (II) is represented by any one of the following general formulae (VIII) to (XI).

[Chem. 19]

General formula (VIII)

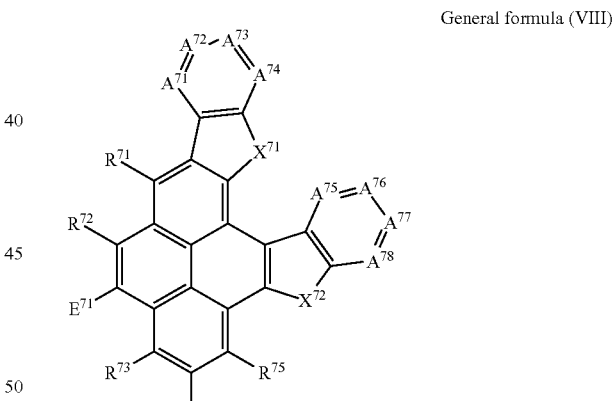

General formula (IX)

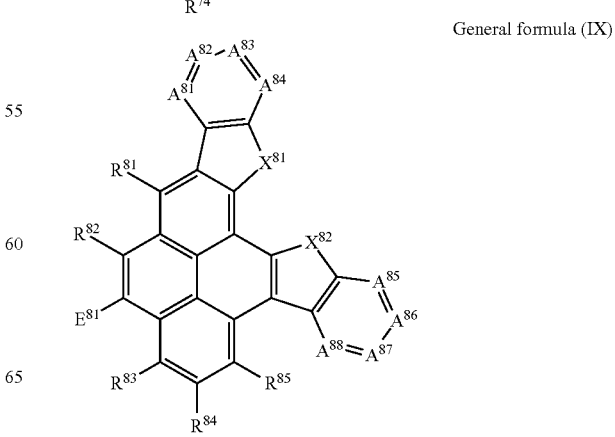

-continued

General formula (X)

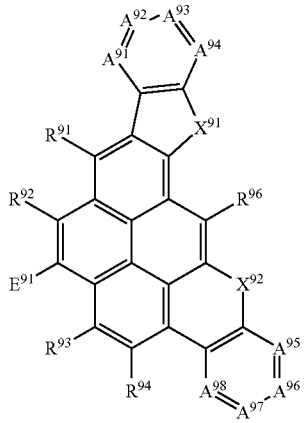

General formula (XI)

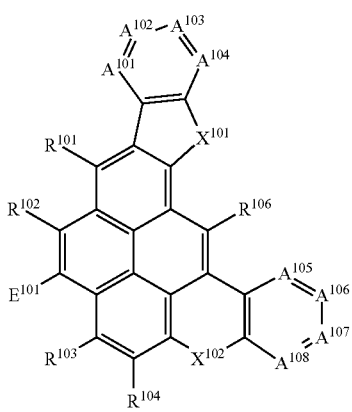

In the general formulae (VIII) to (XI), $R^{71}$ to $R^{106}$ and $E^{72}$ to $E^{102}$ each independently represent a hydrogen atom or a substituent, but there is no case where two adjacent groups out of $R^{71}$ to $R^{106}$ and $E^{72}$ to $E^{102}$ are bonded to each other to form a ring. $X^{72}$ to $X^{102}$ represent any linking group of $CR^{111}R^{112}$, $NR^{113}$, O, S, and $SiR^{114}R^{115}$. $R^{111}$ to $R^{115}$ each independently represent a hydrogen atom or a substituent. $A^{71}$ to $A^{108}$ each independently represent $CR^{116}$ or N. $R^{116}$ represents a hydrogen atom or a substituent, and when two adjacent groups out of $A^{71}$ to $A^{108}$ are $CR^{116}$, the two $R^{116}$'s may be bonded to each other to form a ring structure.

The light emitting material represented by the general formula (I) is preferably a compound represented by the following general formula (III).

[Chem. 20]

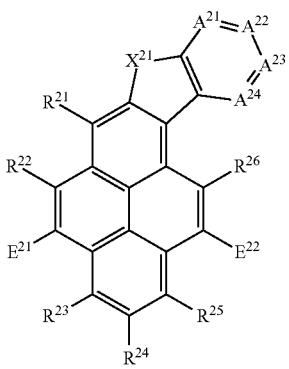

General formula (III)

In the general formula (III), $R^{21}$ to $R^{26}$ each independently represent a hydrogen atom or a substituent, but there is no case where two adjacent groups out of $R^{21}$ to $R^{26}$ are bonded to each other to form a ring.

$E^{21}$ and $E^{22}$ each independently represent a hydrogen atom or a substituent. The members of only one set of $E^{21}$ and $R^{22}$, $E^{21}$ and $R^{23}$, $E^{22}$ and $R^{26}$, and $E^{22}$ and $R^{25}$ are bonded to each other to form a structure represented by the following general formula (E-1) and the members of the other sets are not bonded to each other to form a ring.

[Chem. 21]

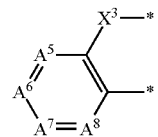

General formula (E-1)

* represents a position for bonding to the pyrene skeleton.

$X^{21}$ and $X^2$ each independently represent any one any linking group of $CR^{111}R^{112}$, $NR^{113}$, O, S, and $SiR^{114}R^{115}$. $X^3$ represents any linking group of $CR^{111}R^{112}$, $NR^{113}$, O, S, and $SiR^{114}R^{115}$. $R^{111}$ to $R^{115}$ each independently represent a hydrogen atom or a substituent.

$A^{21}$ to $A^{24}$ and $A^5$ to $A^8$ each independently represent $CR^{116}$ or N. $R^{116}$ represents a hydrogen atom or a substituent, and when two adjacent groups out of $A^{21}$ to $A^{24}$ and $A^5$ to $A^8$ are $CR^{116}$, the two $R^{116}$'s may be bonded to each other to form a ring structure.

The preferred ranges of $R^{21}$ to $R^{26}$, $E^{21}$, $E^{22}$, $X^3$, $R^{111}$ to $R^{115}$, $A^{21}$ to $A^{24}$, and $A^5$ to $A^8$ in the general formula (III) are the same as the preferred ranges of $R^1$ to $R^6$, $E^1$, $E^2$, $X^3$, $R^{111}$ to $R^{115}$, $A^1$ to $A^4$, and $A^5$ to $A^8$ in the general formula (I).

Specific examples of the light emitting material represented by any one of the general formula (I) are shown below, but it should not be construed that the light emitting material represented by the general formula (I) which can be used in the present invention is limited to the specific examples.

[Chem. 22-1]
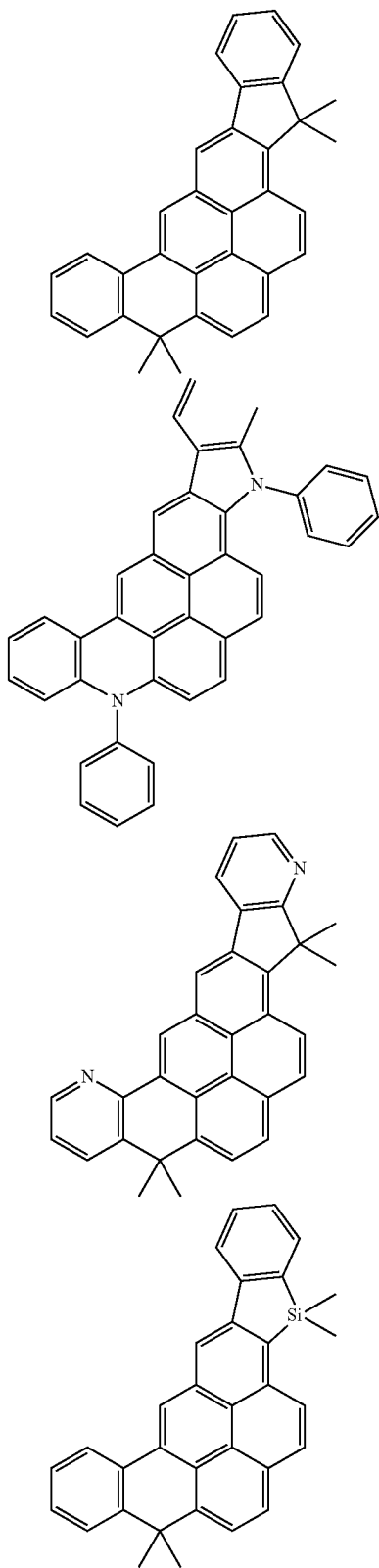
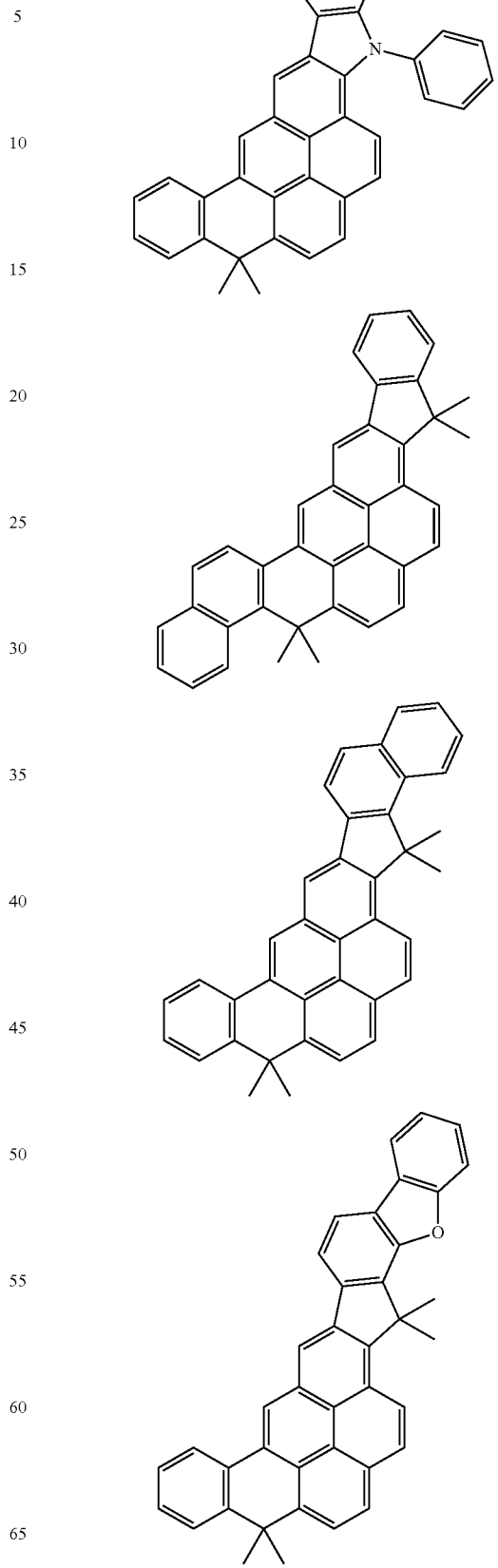

25
-continued
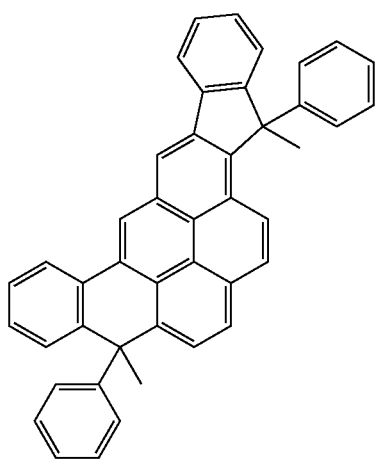
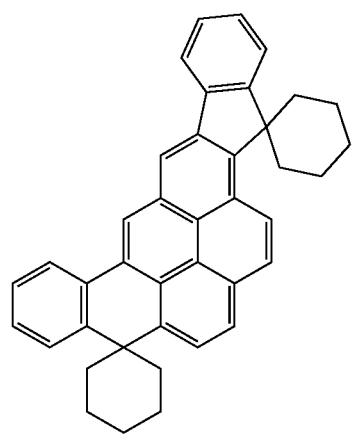
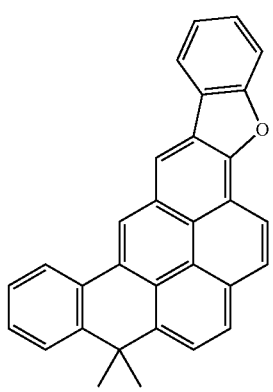
26
-continued
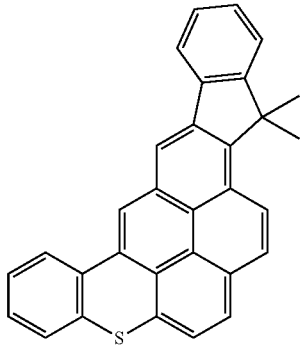
[Chem. 22-2]
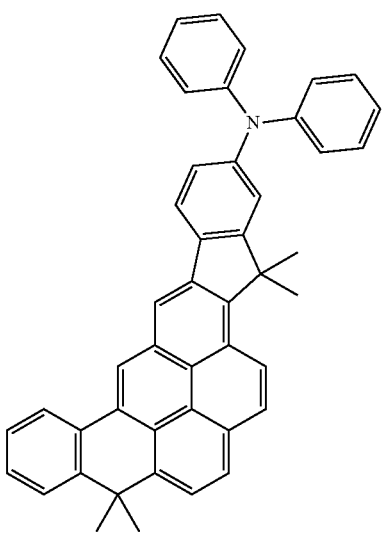
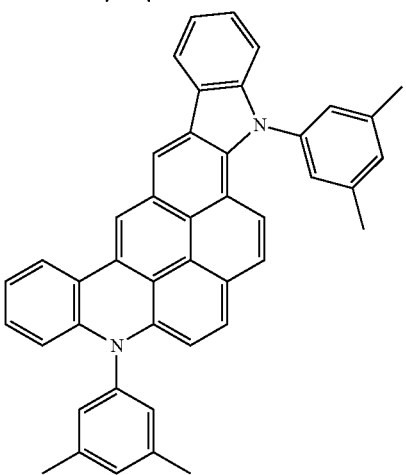

-continued
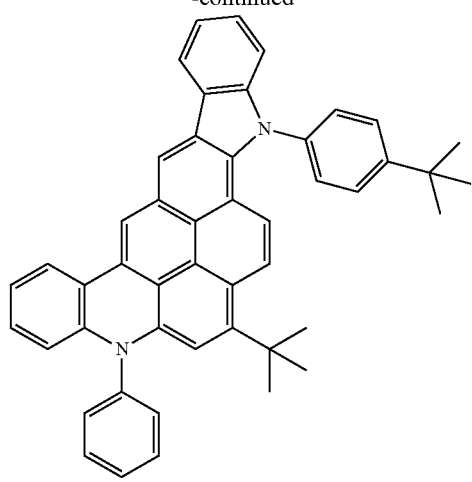
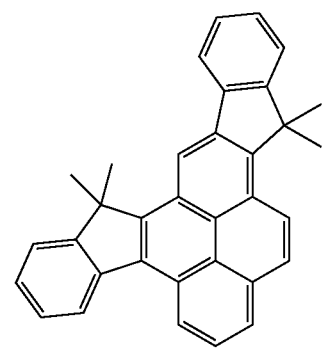
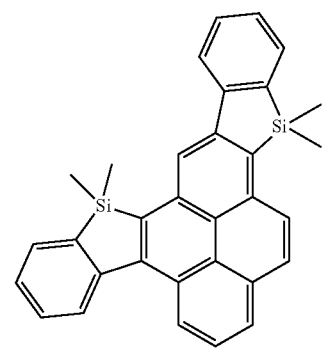
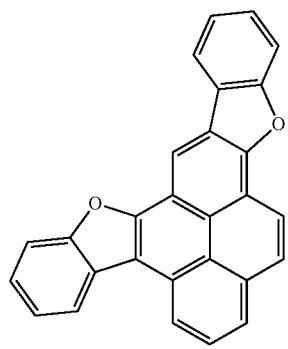
-continued
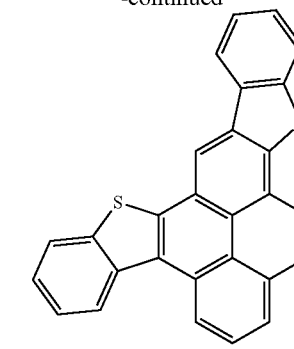
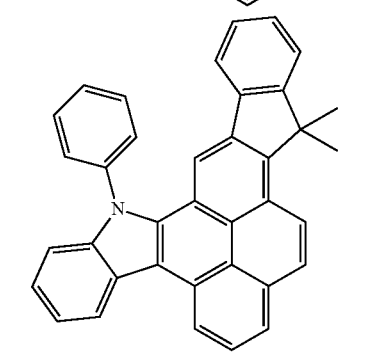
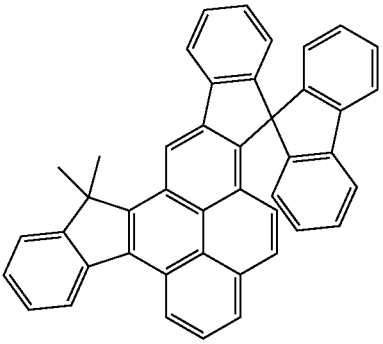
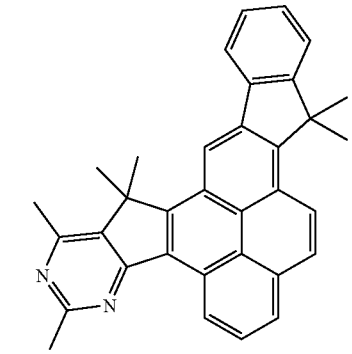
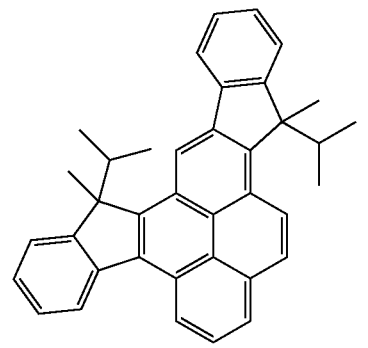

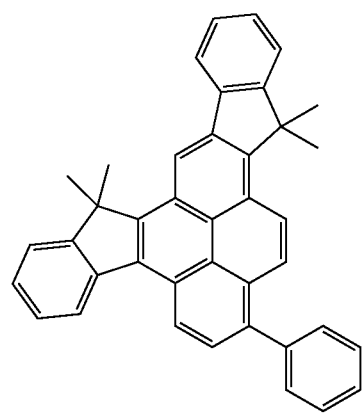
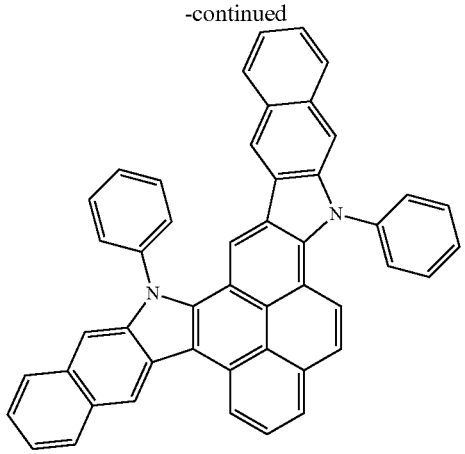

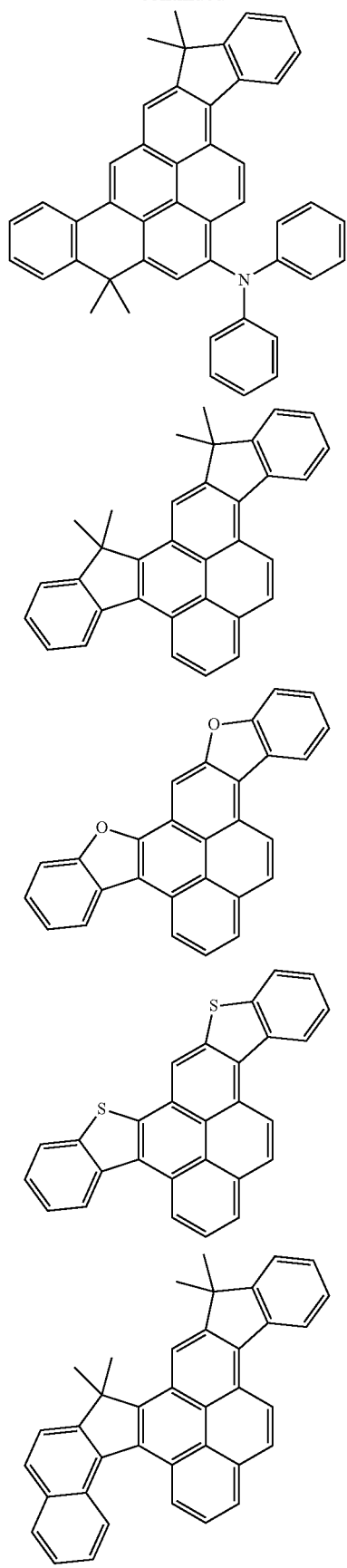
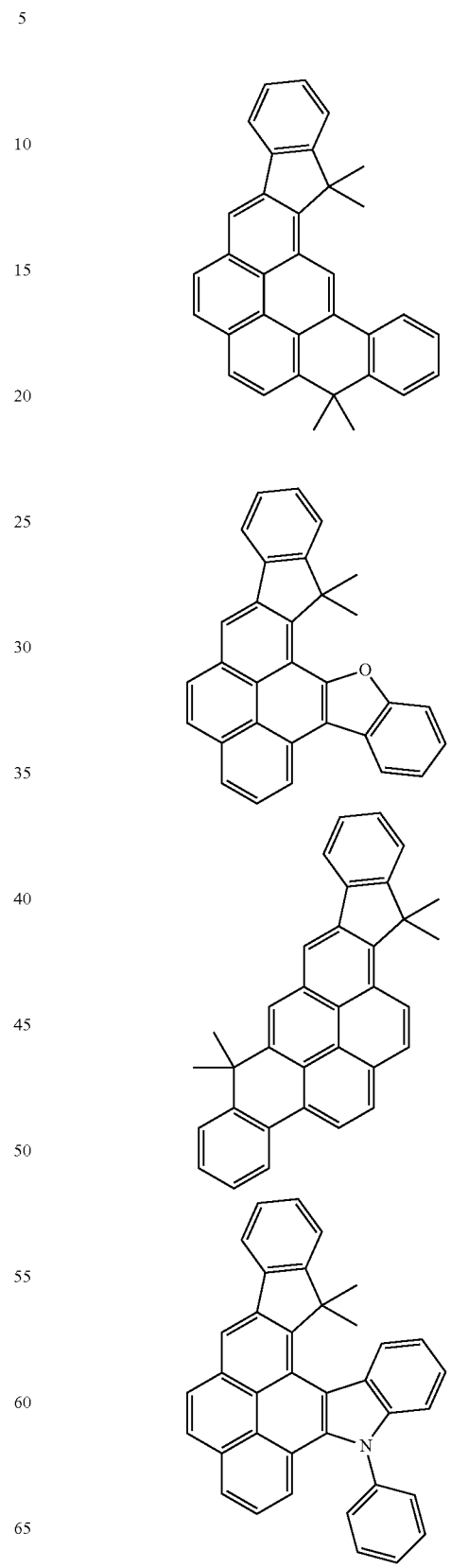

-continued
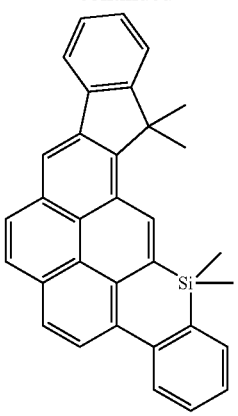
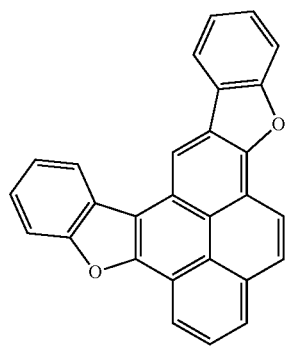
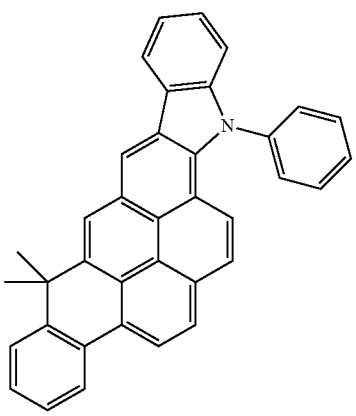
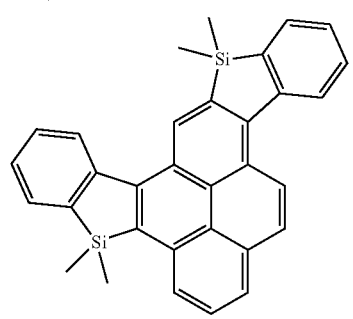
-continued
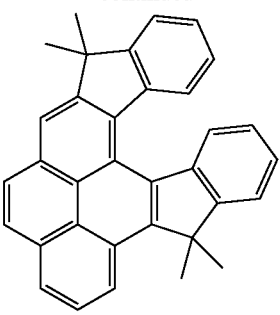
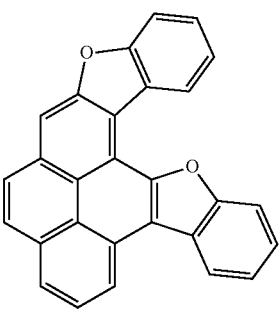
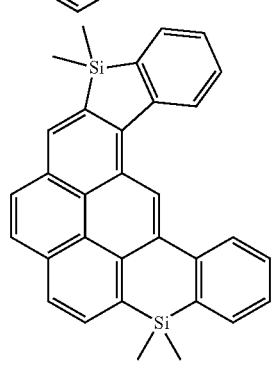
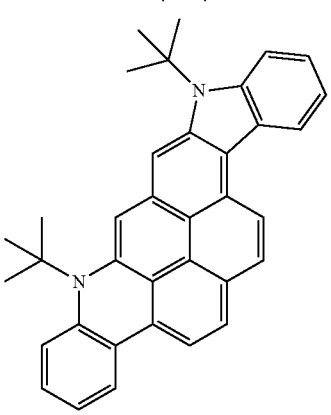
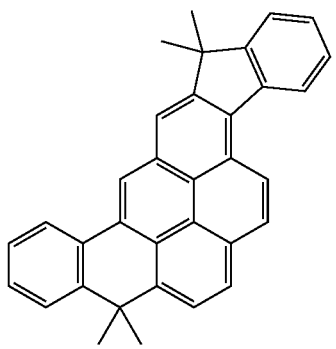

-continued

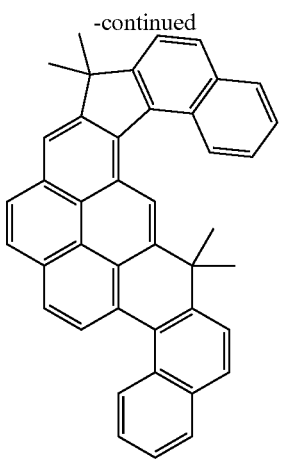

The compound represented by the general formula (I) can be synthesized by a combination of known reactions. It is possible to synthesize the compound by, for example, a combination of the following schemes.

The synthesized compound is preferably purified by column chromatography, recrystallization, or the like, and then purified by sublimation purification. By the sublimation purification, organic impurities can be separated and inorganic salts, residual solvents, or the like can be removed effectively.

When the compounds represented by the general formula (I) are used as light emitting material, the maximum light emitting wavelength thereof is preferably less than 455 nm, more preferably 400 nm or more and less than 455 nm, particularly preferably 420 nm or more and less than 455 nm, still more preferably 430 nm or more and less than 455 nm, and most preferably 440 nm or more and less than 455 nm.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which the light emitting layer includes a compound represented by the general formula (I).

The configuration of the organic electroluminescent element of the present invention is not particularly limited. FIG. 1 shows one example of the configuration of the organic electroluminescent element of the present invention. The organic electroluminescent element 10 in FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed descriptions described in this publication can be applied to the present invention.

Hereinafter, preferred aspects of the organic electroluminescent element of the present invention will be described in detail in the order of the substrate, the electrodes, the organic layer, a protective layer, a sealing enclosure, a driving method, a light emitting wavelength, and applications.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element of the present invention has one or a plurality of organic layers disposed between the electrodes, in which the organic layer includes a light emitting layer, and the light emitting layer includes a host material and at least one compound represented by the general formula (1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in detail in order.

(Configuration of Organic Layer)

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (I) is contained in at least one or two or more organic layers disposed between the electrodes of the organic electroluminescent element. The compound represented by the general formula (I) is particularly preferably contained in the light emitting layer. However, so far as the gist of the present invention is not deviated, the compound represented by the general formula (I) may be contained in an organic layer other than the light emitting layer of the organic electroluminescent element of the present invention. Examples of the organic layer other than the light emitting layer, which may contain the compound represented by the general formula (I), include a hole injecting layer, a hole transporting layer, an electron transporting layer, an electron injecting layer, an exciton blocking layer, and a charge blocking layer (a hole blocking layer, an electron blocking layer, and the like), preferably any one of an exciton blocking layer, a charge blocking layer, an electron transporting layer, and an electron injecting layer, and more preferably an exciton blocking layer, a charge blocking layer, or an electron transporting layer.

In the case where the compound represented by the general formula (I) is contained in the light emitting layer, the compound represented by the general formula (I) is contained in the light emitting layer, preferably in the amount of 0.1% by mass to 100% by mass, more preferably 1% by mass to 50% by mass, and still more preferably 2% by mass to 20% by mass, with respect to the total mass.

In the case where the compound represented by the general formula (I) is contained in an organic layer other than the light emitting layer, the compound represented by the general formula (I) is contained in the light emitting layer, preferably in the amount of 70% by mass to 100% by mass, more preferably 80% by mass to 100% by mass, and still more preferably 90% by mass to 100% by mass, with respect to the total mass.

(Method for Forming Organic Layer)

The respective organic layers in the organic electroluminescent element of the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element of the present invention, the organic layer disposed between the pair of electrodes is preferably formed by deposition of a composition further including at least the compound represented by the general formula (I).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, the light emitting layer contains the compound represented by the general formula (I), and it is a preferred aspect to use the compound represented by the general formula (I) as a light emitting material of the light emitting layer. Here, the host material as referred to in the present specification is a compound which chiefly plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element. The compound represented by the general formula (I) may be used as a host material of the light emitting layer.

(Light Emitting Material)

In the organic electroluminescent element of the present invention, the compound represented by the general formula (I) is preferably used as the light emitting material, but in this case, a combination of the compound with light emitting materials different from the compound represented by the general formula (I) can be used. Further, in the organic electroluminescent element of the present invention, in the case where the compound represented by the general formula (I) is used as a host material of the light emitting layer or in the case where the compound represented by the general formula (I) is used in an organic layer other than the light emitting layer, a light emitting material other than the compound represented by the general formula (I) can be used in the light emitting layer.

The light emitting material which can be used in the present invention may be a phosphorescent light emitting material. Further, the light emitting layer in the present invention may contain two or more kinds of light emitting materials in order to improve the color purity or widen the light emitting wavelength region.

The fluorescent light emitting material and the phosphorescent material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, the detailed descriptions thereon in these publications can be applied to the present invention.

The kind of the fluorescent light emitting material which can be used in the present invention is not particularly limited, but examples thereof include those other than the compound represented by the general formula (1-1), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

In addition, the light emitting layer may be made of a single layer or two or more layers. The respective layers may include the same light emitting materials or host materials, and may also include different materials from each other over layers. In the case where a plurality of light emitting layers are present, the respective light emitting layers may emit light in different luminous colors from each other.

(Host Material)

The host material is a compound that usually plays a role in injecting or transporting charges in the light emitting layer and is also a compound which does not substantially emit light in itself. As used herein, the statement "which does not substantially emit light" means that the amount of light emitting from the compound which does not substantially emit light is preferably 5% or less, more preferably 3% or less, and still more preferably 1% or less of the total amount of light emitting in the entirety of the element.

Examples of the host material which can be used in the organic electroluminescent element of the present invention include the following compounds:

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused ring aromatic hydrocarbon compounds (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

In the organic electroluminescent element of the present invention, the host material included in the light emitting layer preferably has a hydrocarbon fused ring structure having 10 to 50 carbon atoms.

The hydrocarbon fused ring structure having 10 to 50 carbon atoms is preferably naphthalene, phenanthrene, benzo[c]phenanthrene, anthracene, pyrene, triphenylene, or chrysene, more preferably naphthalene, phenanthrene, benzo[c]phenanthrene, or anthracene, and most preferably anthracene. Specifically, the hydrocarbon fused ring structure having 10 to 50 carbon atoms in the host material is further preferably an anthracene skeleton. Further, it is particularly preferable that the hydrocarbon fused ring structure having 10 to 50 carbon atoms is a compound composed of only carbon, and hydrogen or deuterium.

The host material that can be used in the light emitting layer in the organic electroluminescent element of the present invention may be a host material having hole transporting properties or a host material having electron transporting properties.

In the light emitting layer, the singlet lowest excited energy ($S_1$ energy) in the film state of the host material is preferably higher than the $S_1$ energy of the light emitting material from the viewpoints of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the light emitting material. Further, even in the case where $S_1$ of the host material is higher than the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Furthermore, the content of the host compound in the light emitting layer in the organic electroluminescent element of the present invention is not particularly limited, but from the viewpoint of luminous efficiency and driving voltage, it is preferably from 15% by mass to 95% by mass, with respect to the total mass of the compounds forming the light emitting layer. When the light emitting layer includes a plurality of kinds of host compounds containing the compound represented by the general formula (I), the content of the compound represented by the general formula (I) is preferably from 50% by mass to 99% by mass, with respect to the total host compounds of the compound.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, Anode/hole injecting layer/hole transporting layer/blocking layer/light emitting layer/blocking layer/electron transporting layer/electron injecting layer/cathode.

The organic electroluminescent element of the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element of the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer preferably includes at least one compound of the compounds represented by the following general formulae (Sa-1), (Sb-1), and (Sc-1).

[Chem. 23]

General formula (Sa-1)

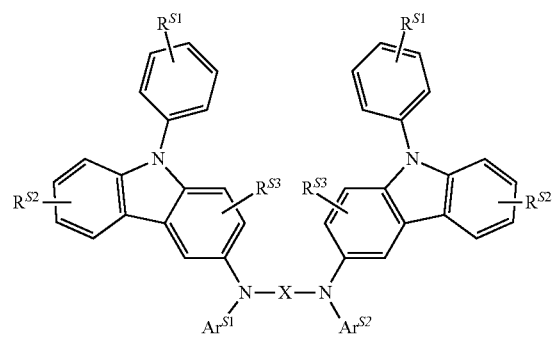

(in which X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 24]

General formula (Sb-1)

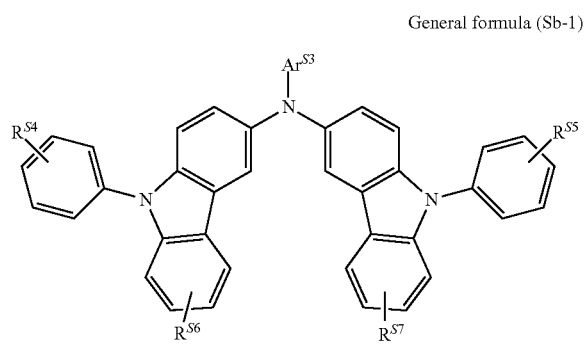

(in which $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 25]

General formula (Sc-1)

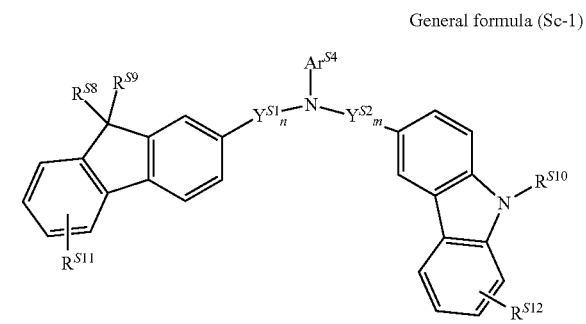

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. X is preferably a substituted or unsubstituted arylene group having 6 to 30 carbon atoms, more preferably having a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms.

$R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene having 1 to 30 carbon atoms, or substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

[Chem. 26]

General formula (Sa-2)

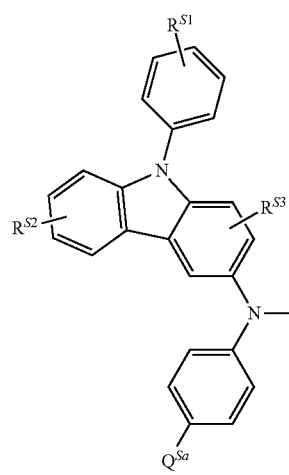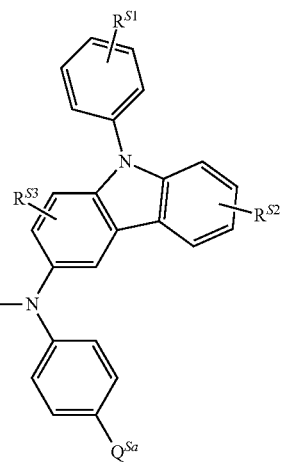

(in which $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

[Chem. 27]

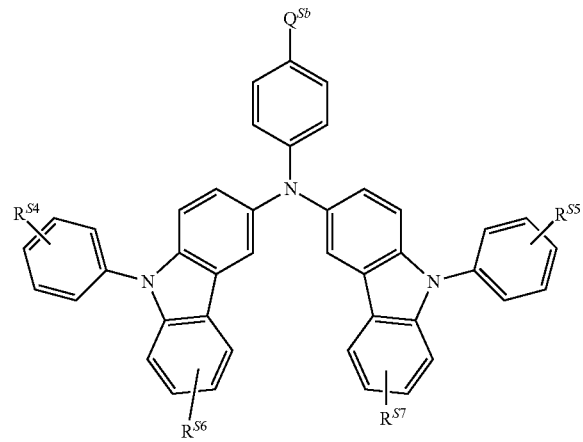

General formula (Sb-2)

(in which $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

[Chem. 28]

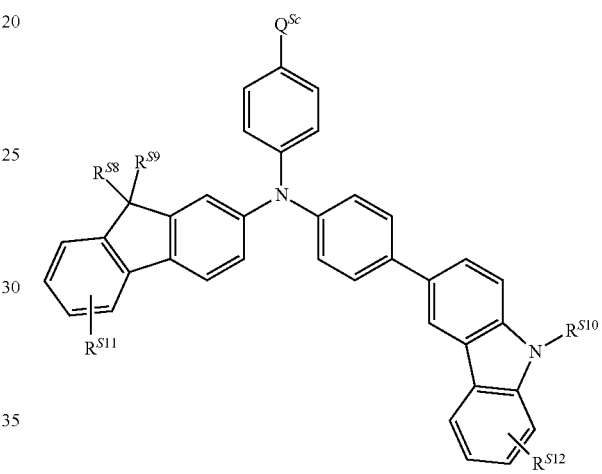

General formula (Sc-2)

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$ and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 29]

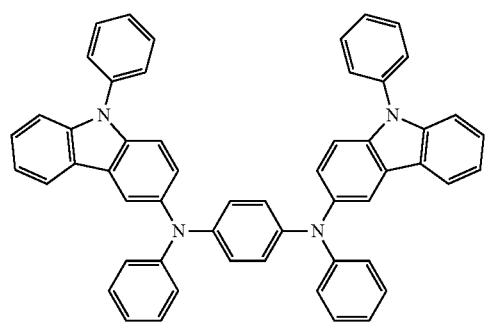

1

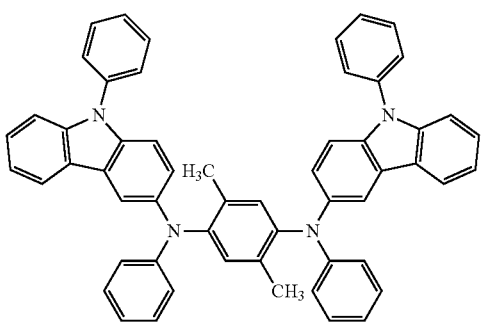

2

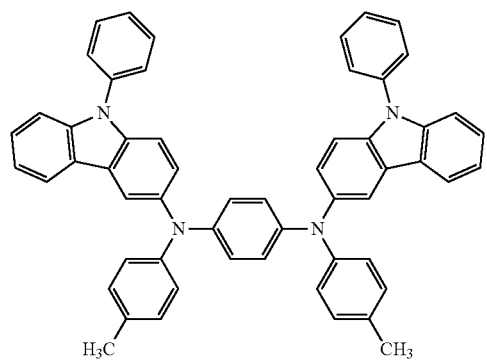

3

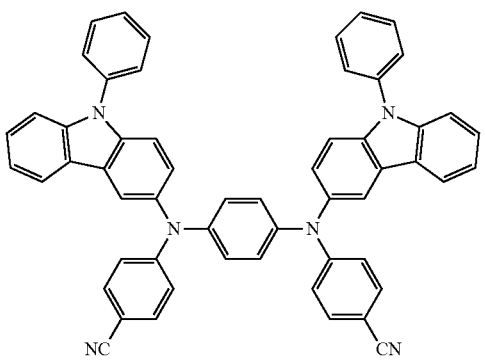

4

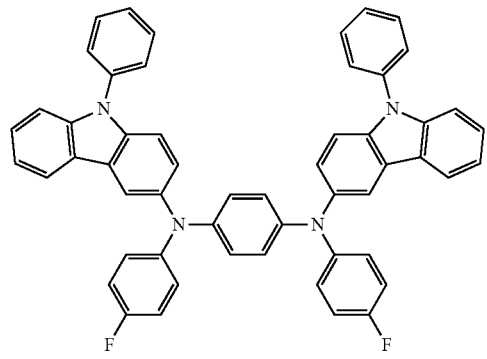

5

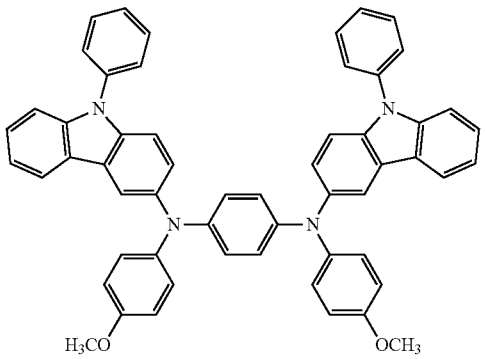

6

-continued
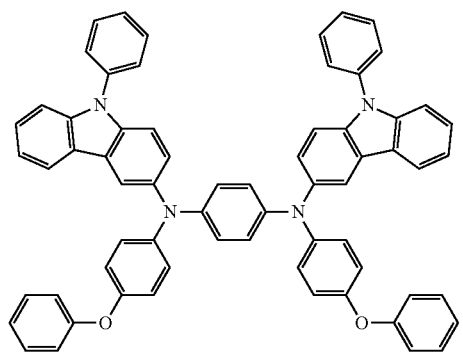
7
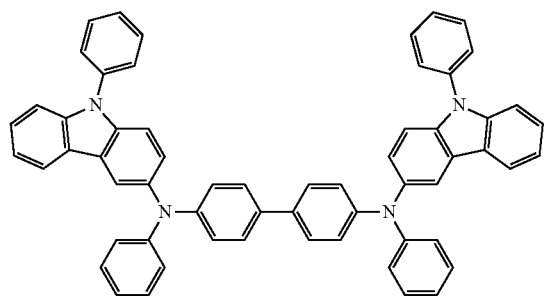
8
[Chem. 30]
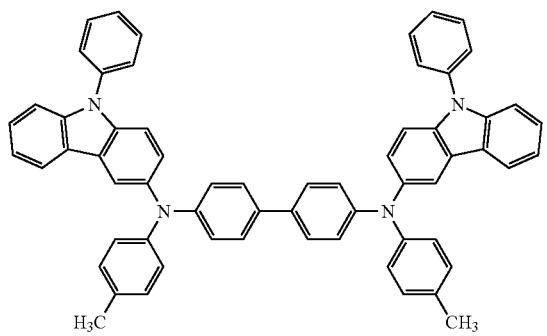
9
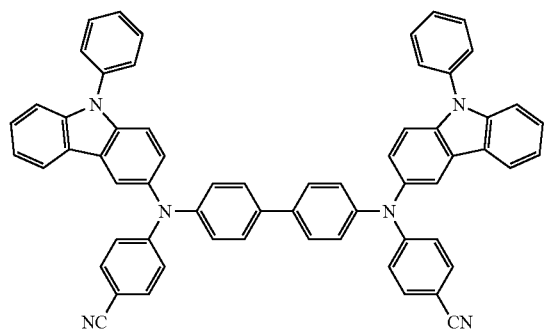
10
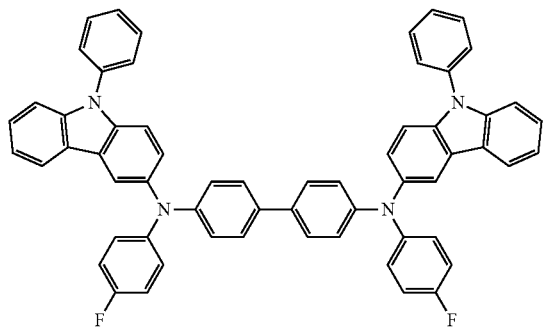
11
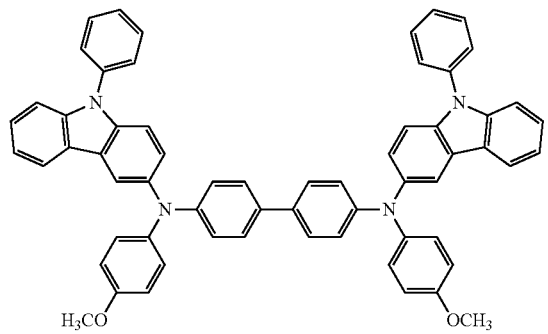
12
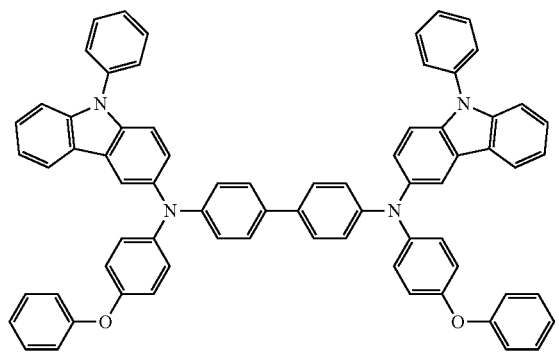
13
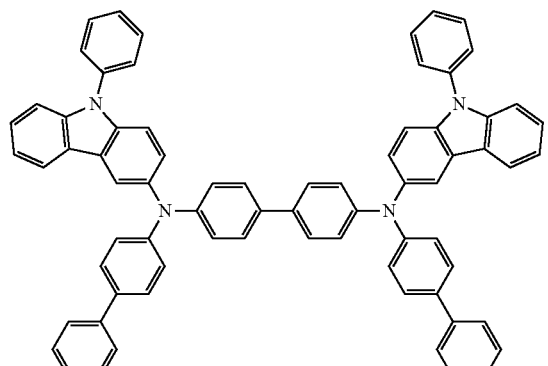
14

[Chem. 31]
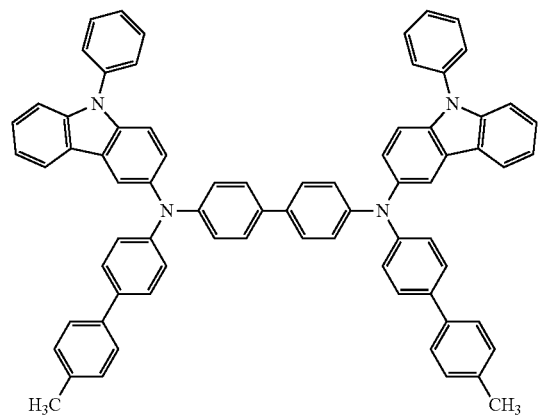
15
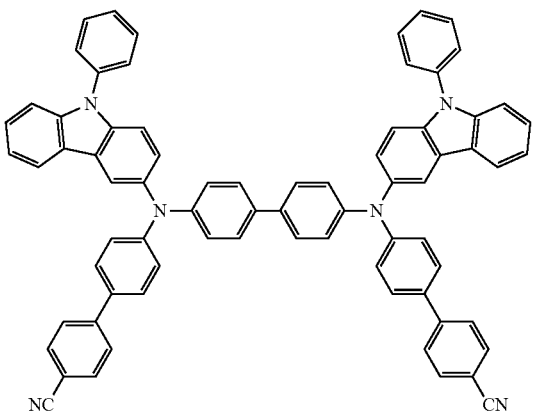
16
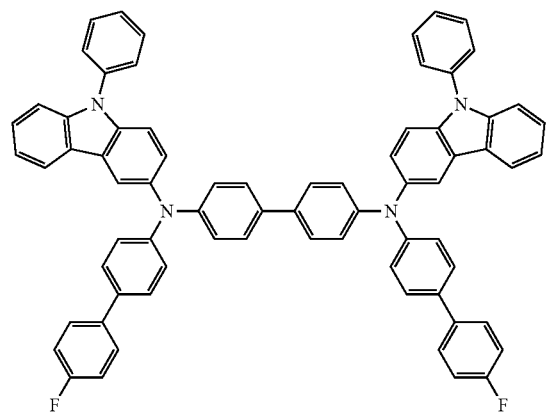
17
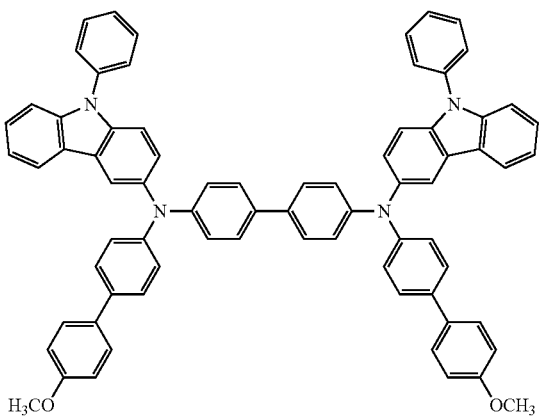
18
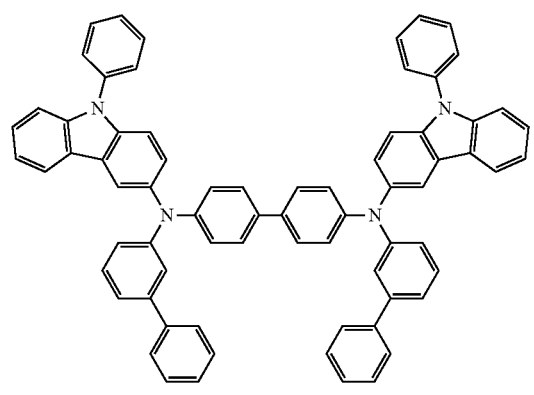
19
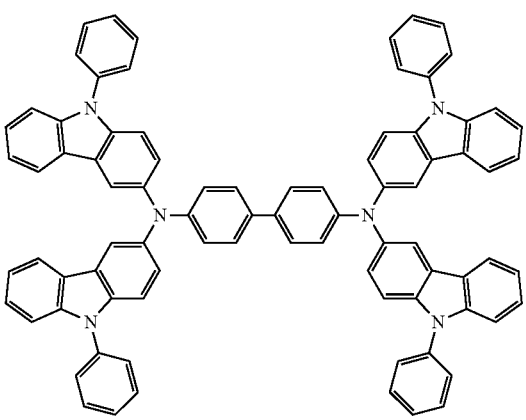
20

-continued
[Chem. 32]
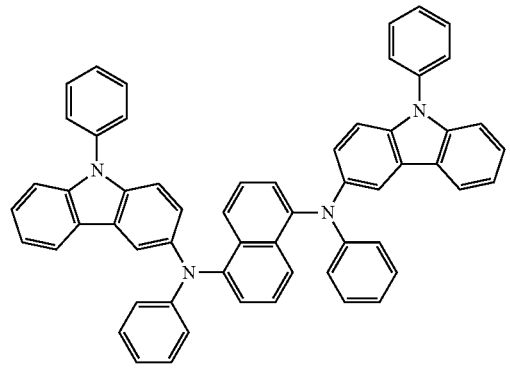
21
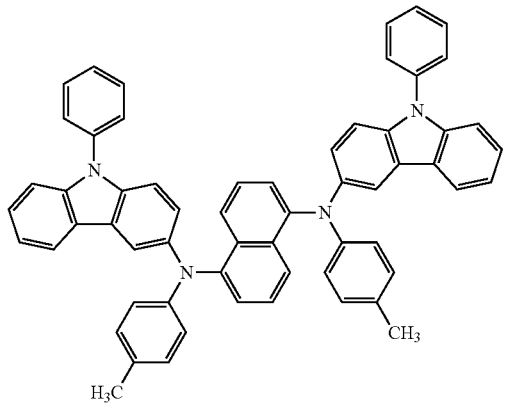
22
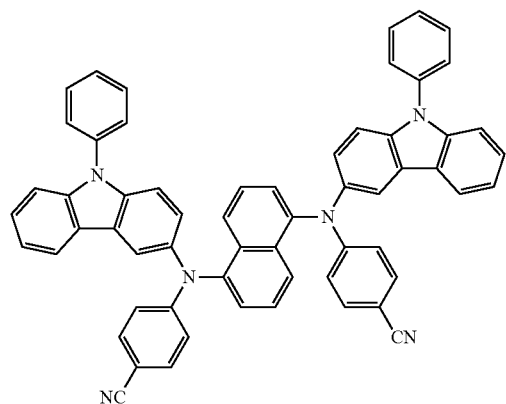
23
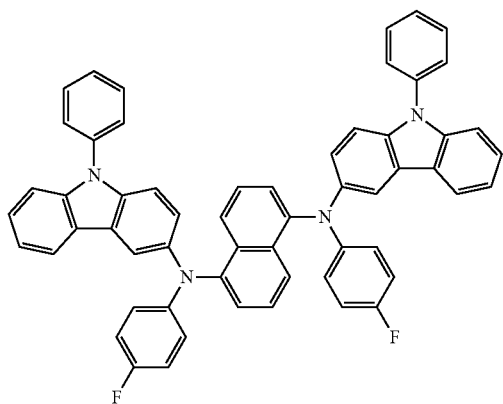
24
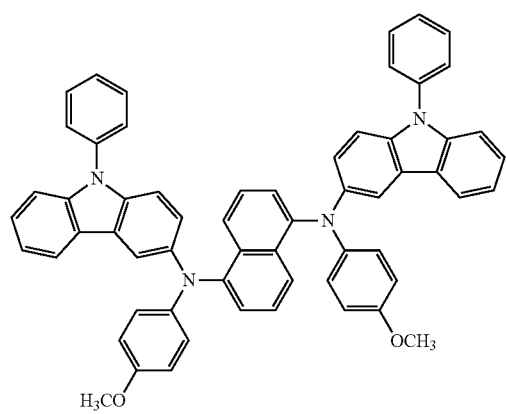
25
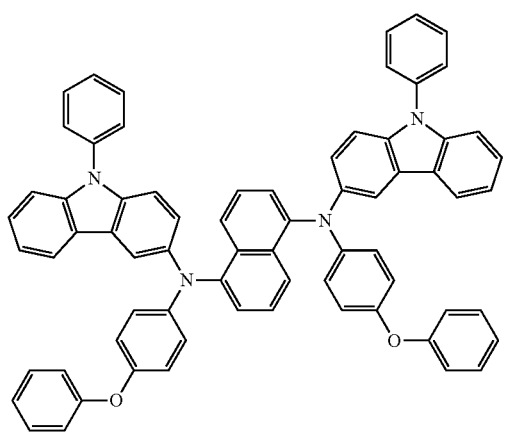
26

[Chem. 33]
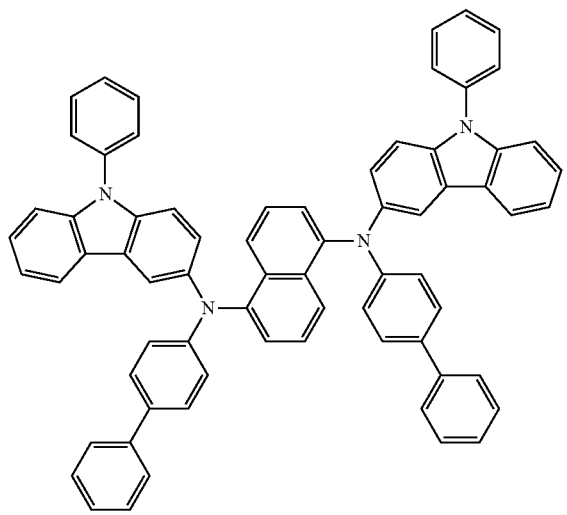
27
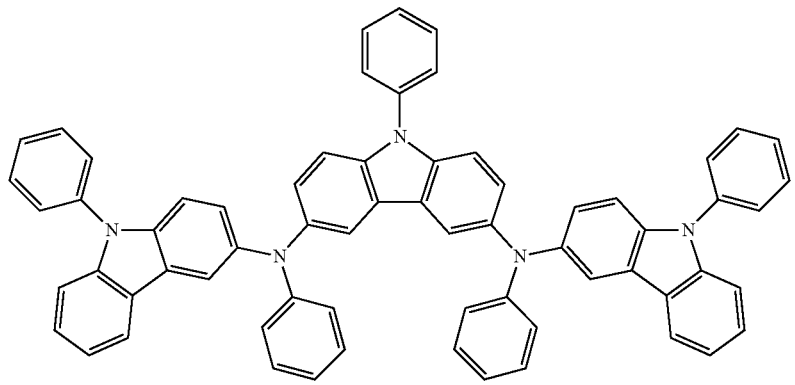
28
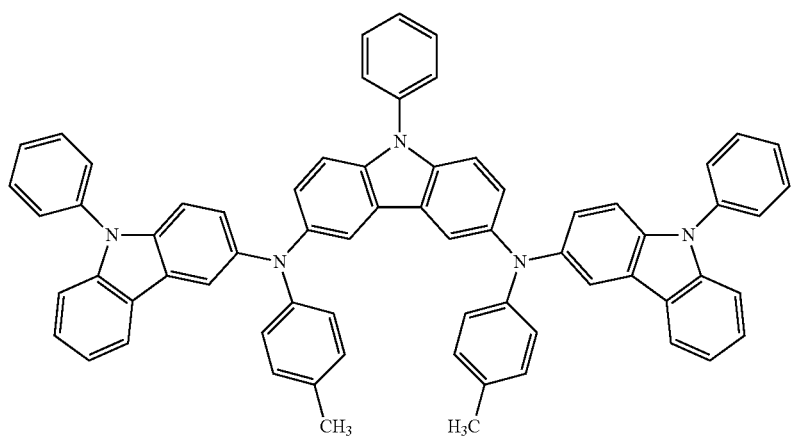
29

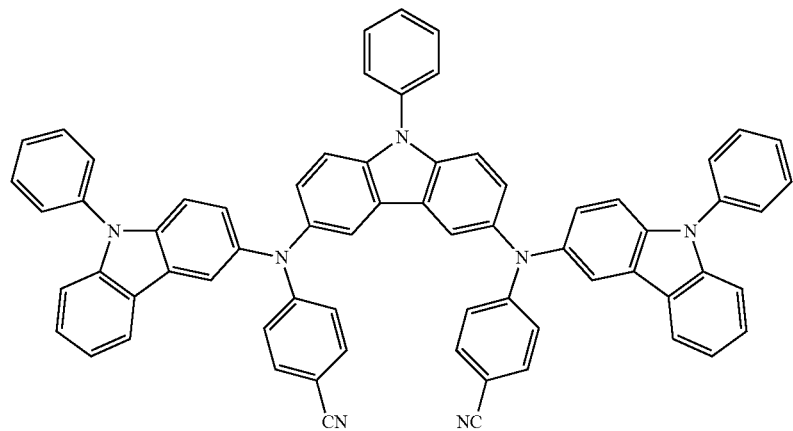
30
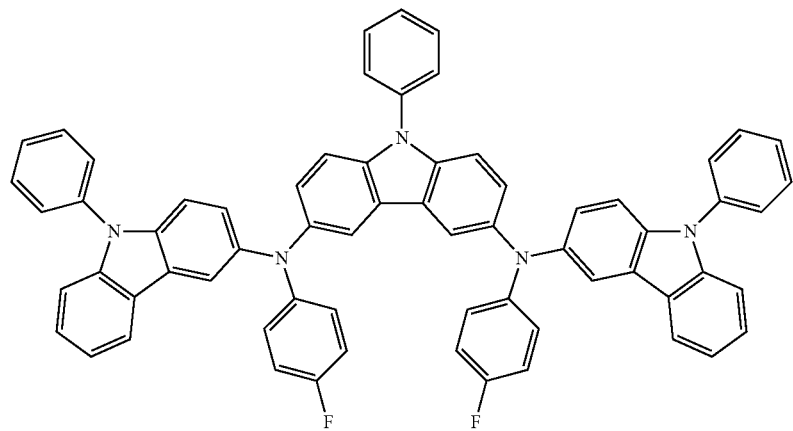
31
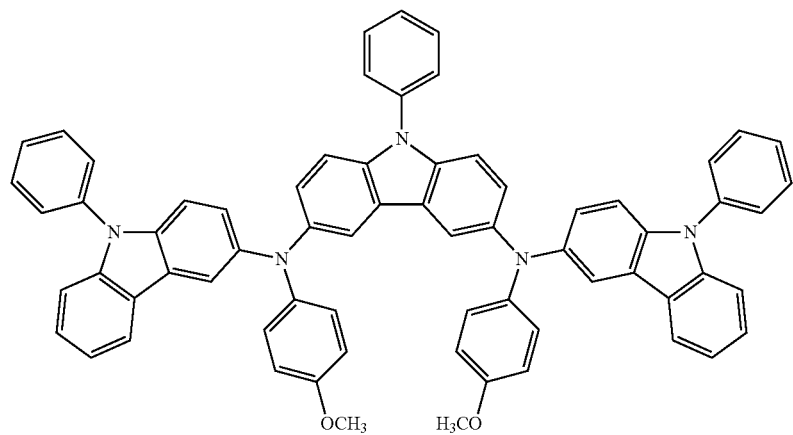
32

[Chem. 34]
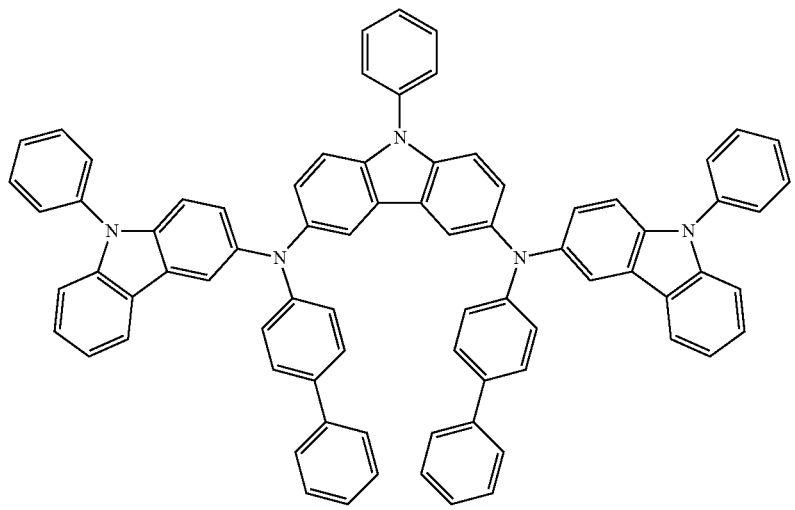
33
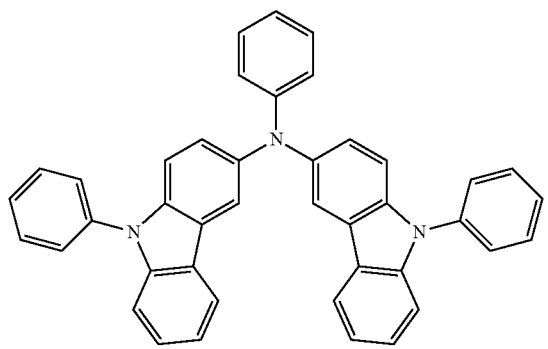
34
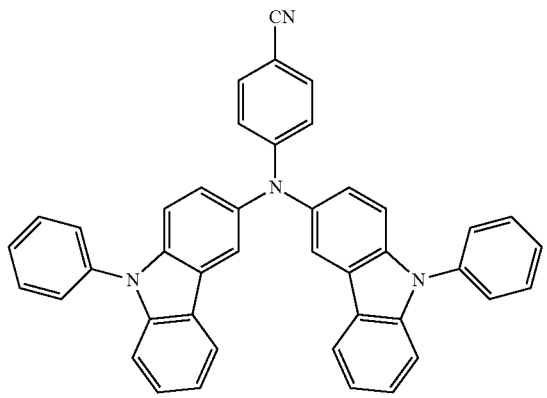
35
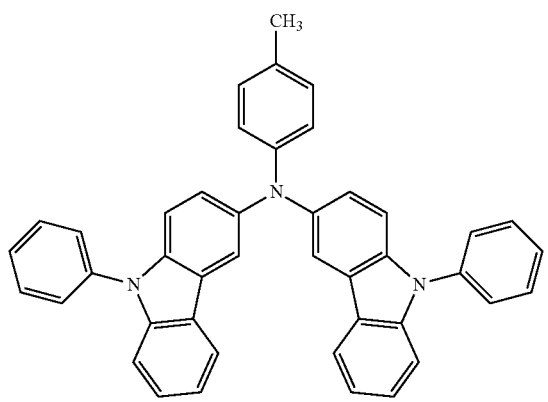
36
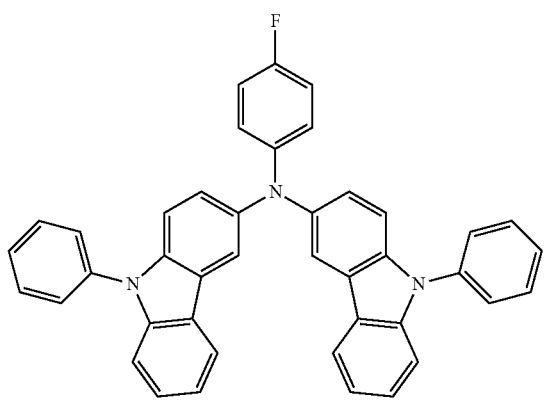
37

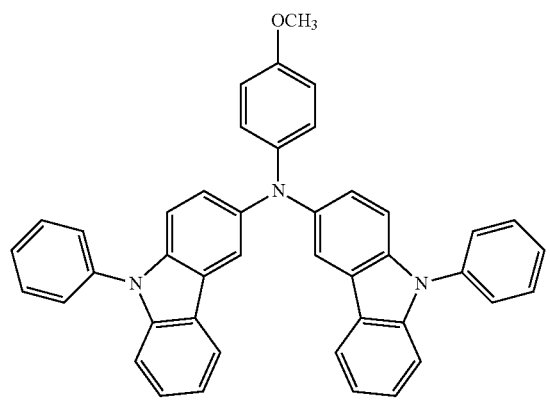
38
[Chem. 35]
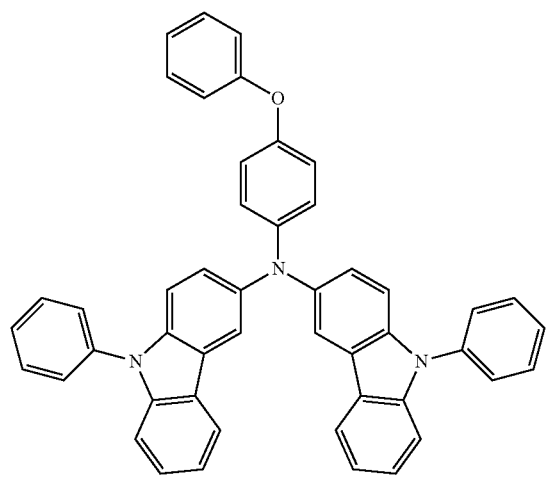
39
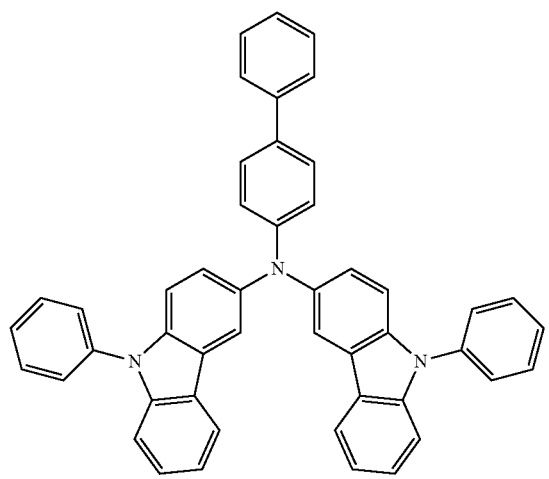
40
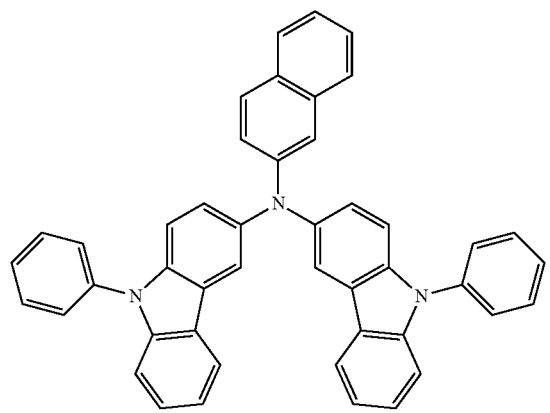
41
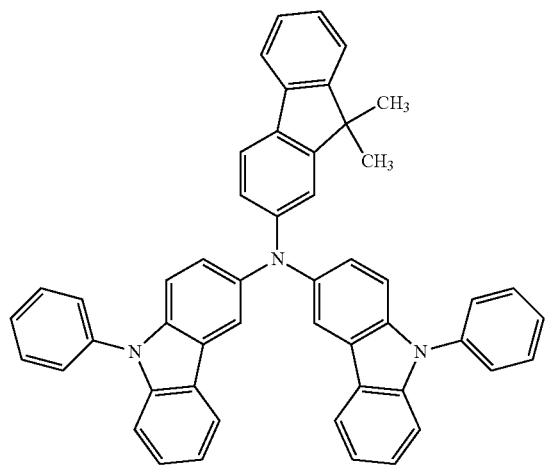
42

[Chem. 36]
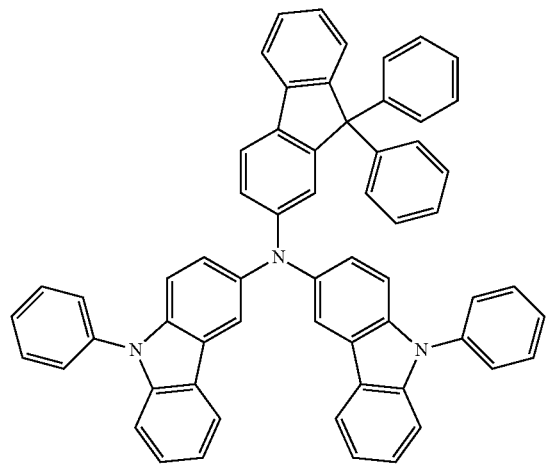
43
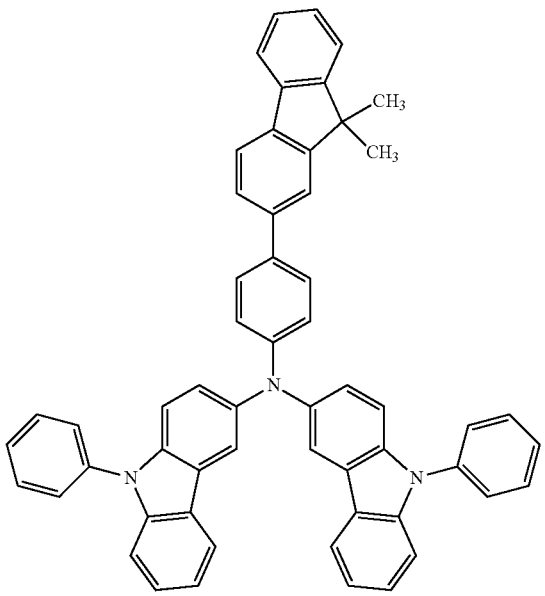
44
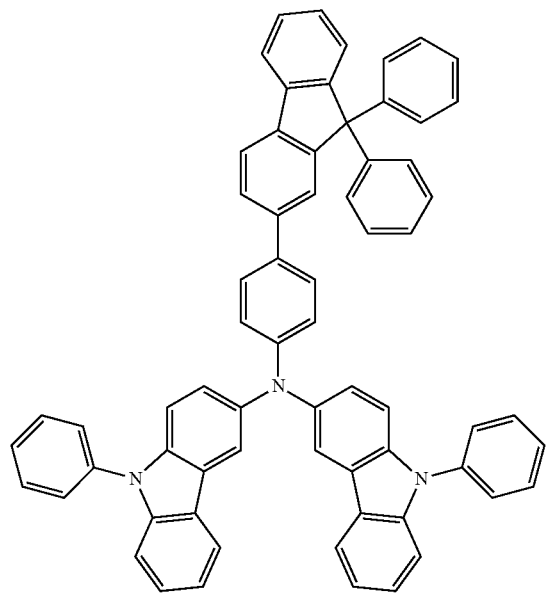
45
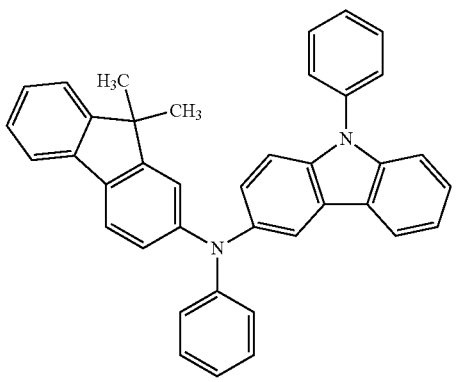
46

[Chem. 37]
47
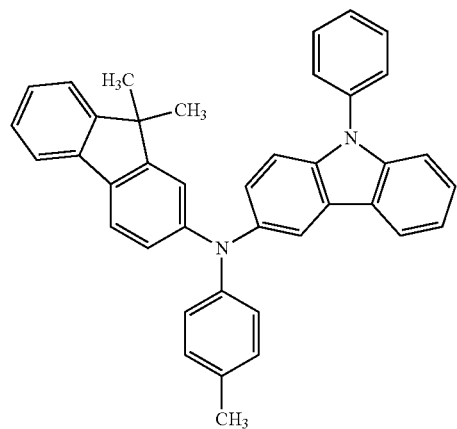
48
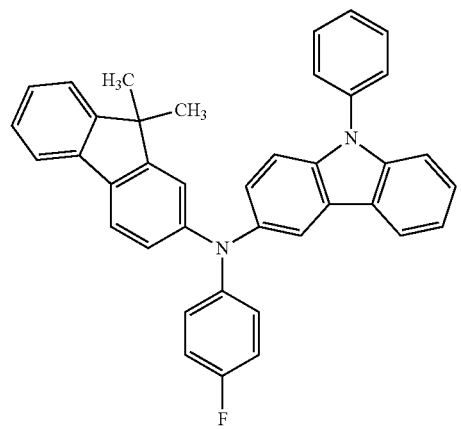
49
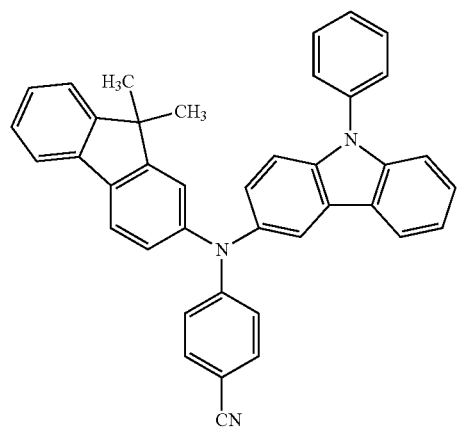
50
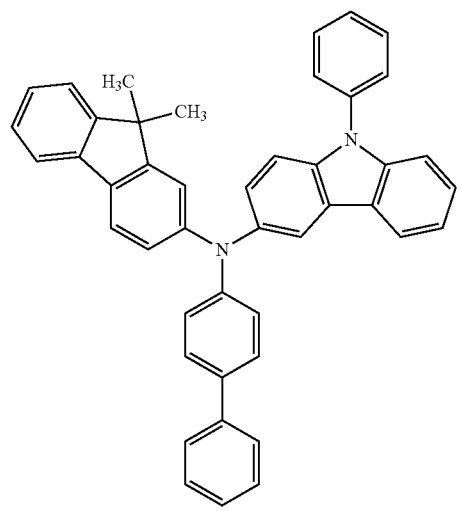
51
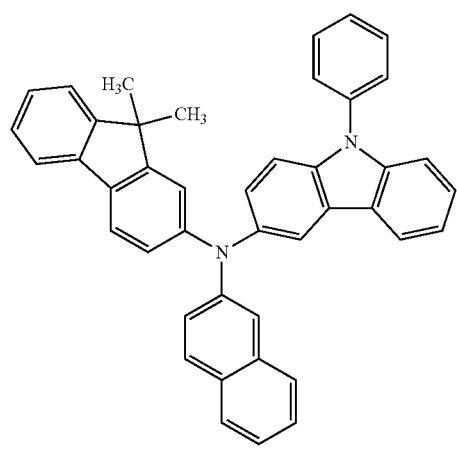
52
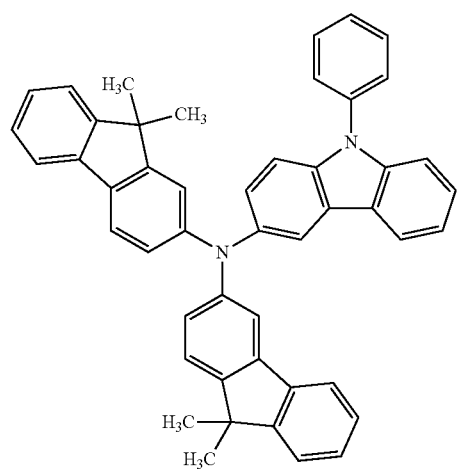

-continued
53
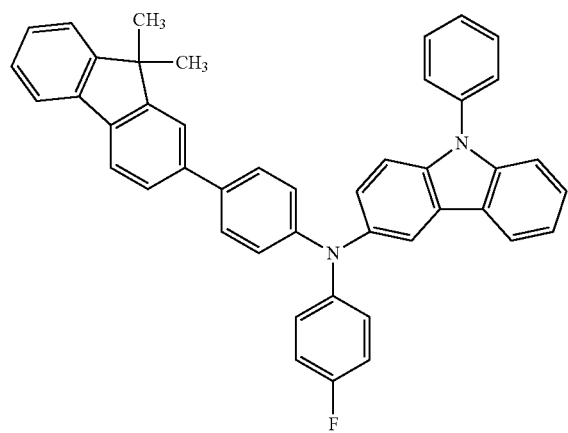
54
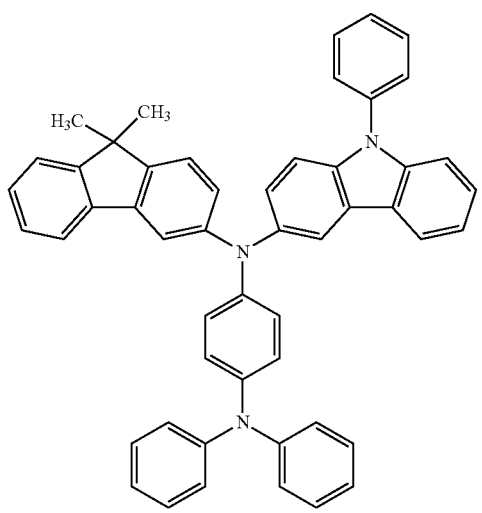
55
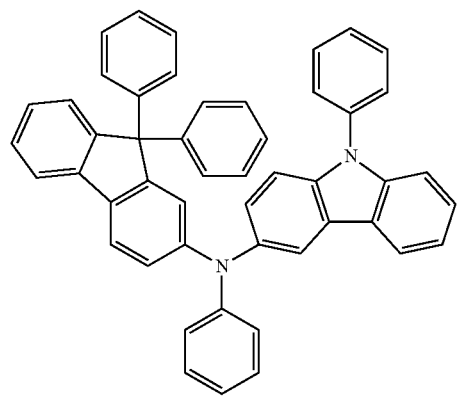
[Chem. 38]
56
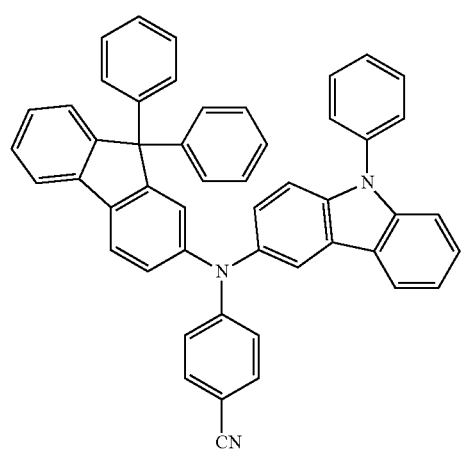
57
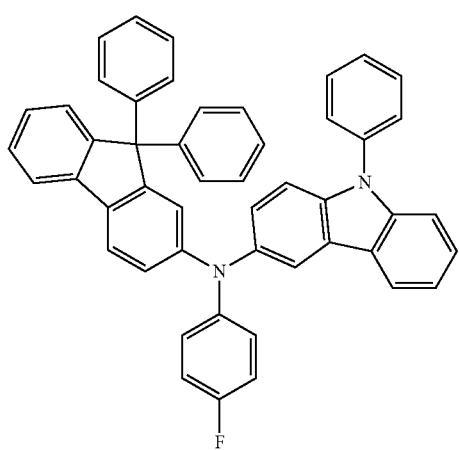

-continued
58
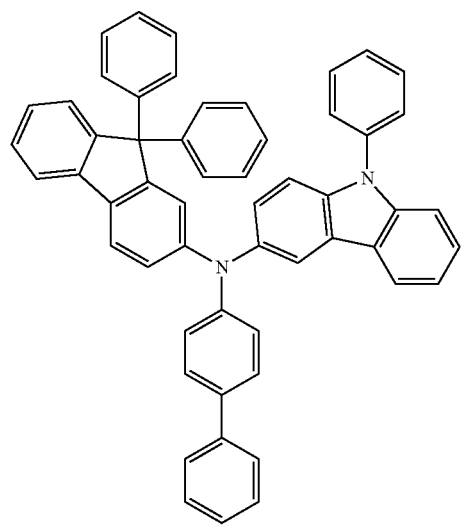
59
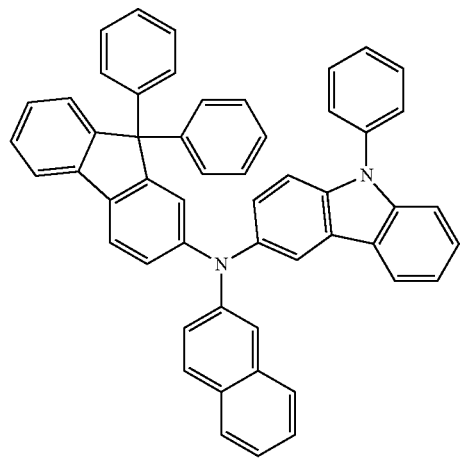
60
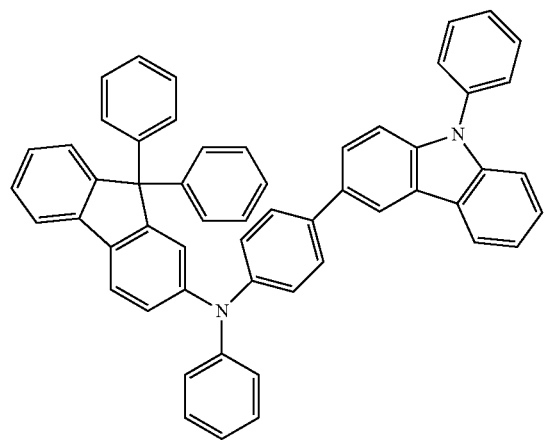
61
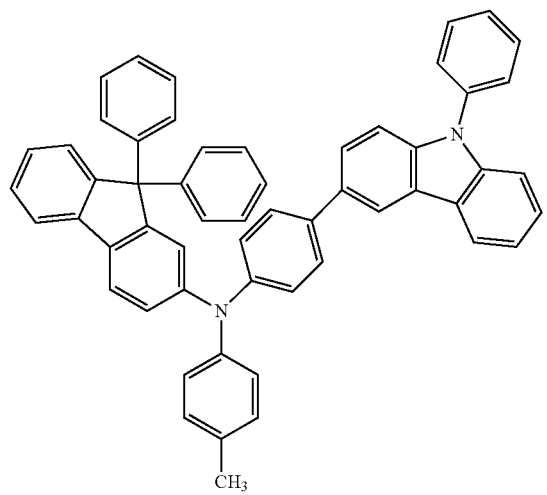
62
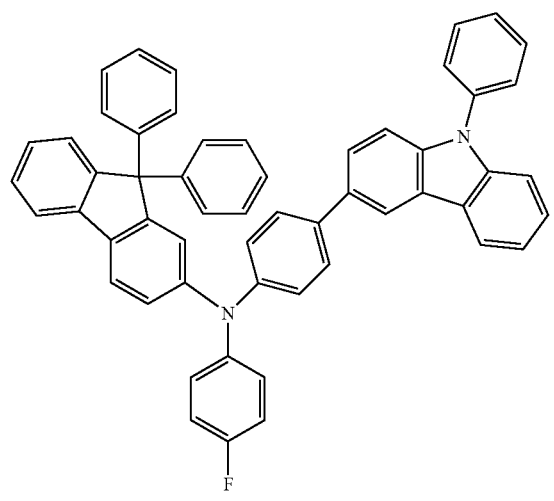
63
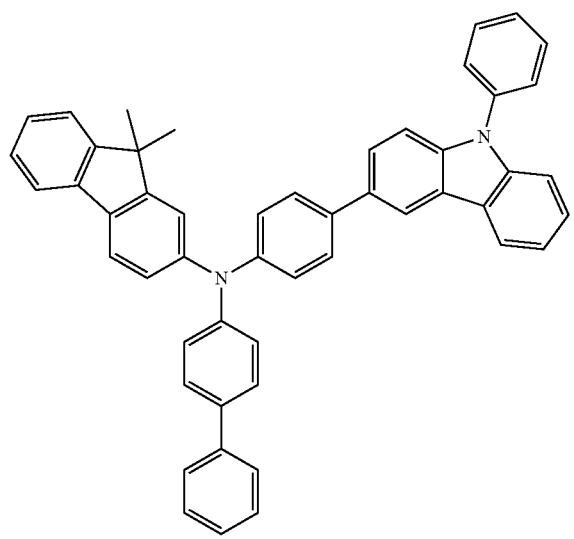

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and above all, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70% by mass to 100% by mass, and more preferably 85% by mass to 100% by mass, with respect to the total mass of the organic layer added.

With respect to the hole injecting layer and the hole transporting layer, the detailed descriptions in paragraph Nos. [0165] to [0167] of JP-A-2008-270736 can be applied to the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include tetracyanoquinodimethane (TCNQ), tetrafluorotetracyanoquinodimethane ($F_4$-TCNQ), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer (A-2) Electron Blocking Layer The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (I) can be used. As the other electron transporting materials, anyone selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (I) can be used.

Examples of the organic compounds constituting the hole blocking layer, other than the compound represented by the general formula (I), include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (I), a compound represented by the following general formula (P-1), and a compound represented by the following general formula (O-1).

Hereinafter, a compound represented by the general formula (O-1) and a compound represented by the general formula (P-1) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element.

Hereinafter, the general formula (O-1) will be described.

[Chem. 39]

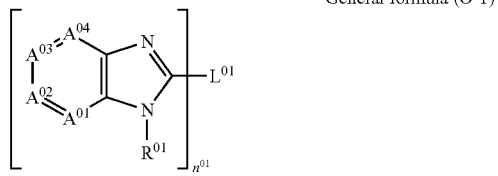

General formula (O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ are C—$R^A$; it is more preferable that $A^{O1}$ be a nitrogen atom, and $A^{O2}$ to $A^{O4}$ be C—$R^A$; it is still more preferable that $A^{O1}$ be a nitrogen atom, $A^{O2}$ to $A^{O4}$ be C—$R^A$, and $R^A$'s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents any of a divalent to hexavalent linking group including an aryl ring (preferably having 6 to 30 carbon atoms) or a heteroaryl ring (preferably having 4 to 12 carbon atoms.) $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 40]

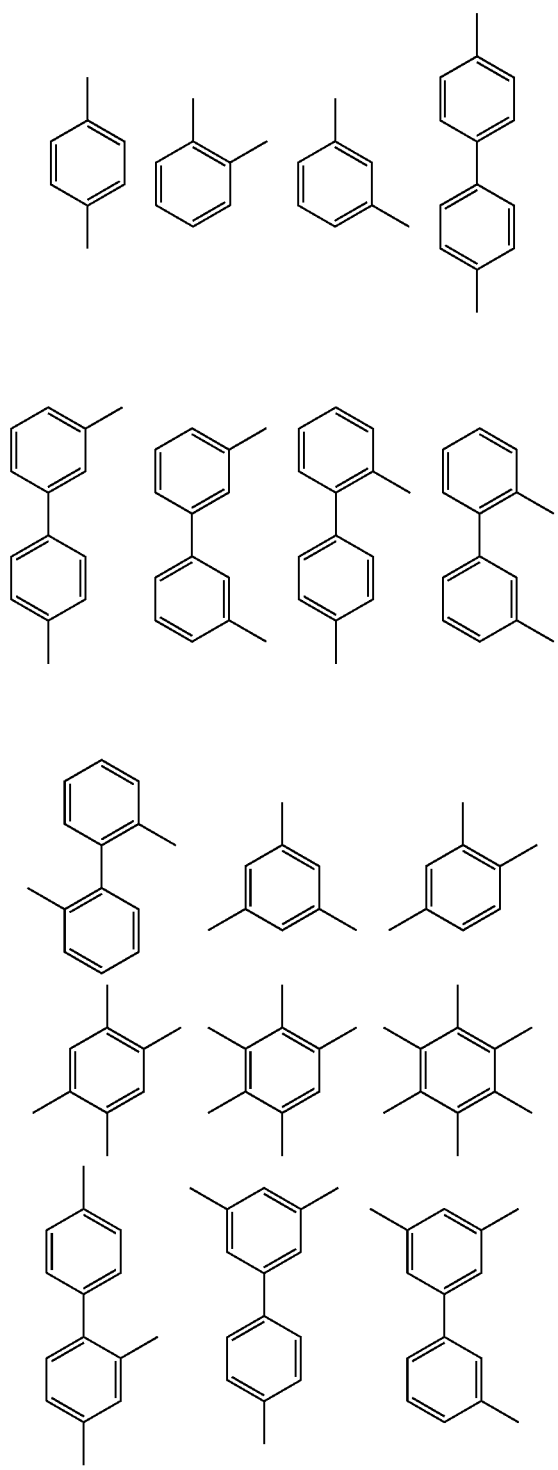

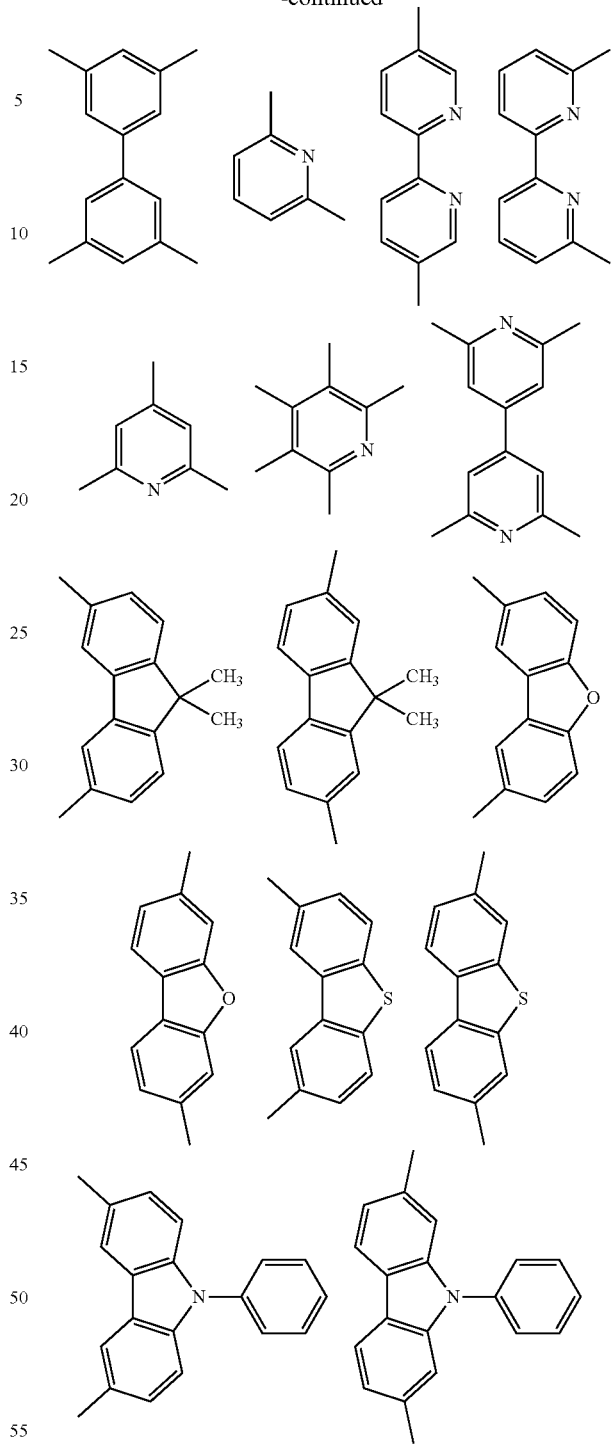

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., and still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 41]

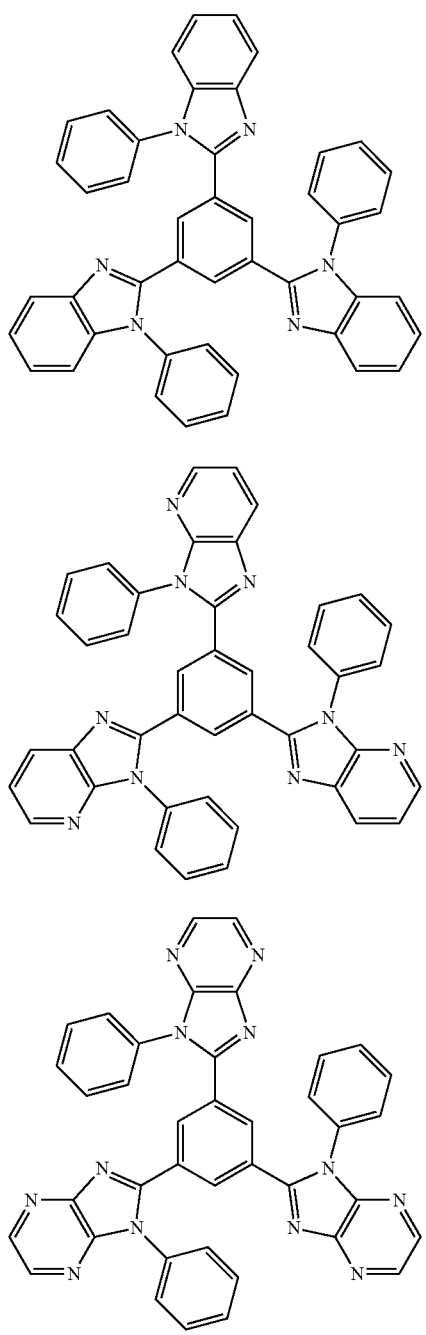

OM-1

OM-2

OM-3

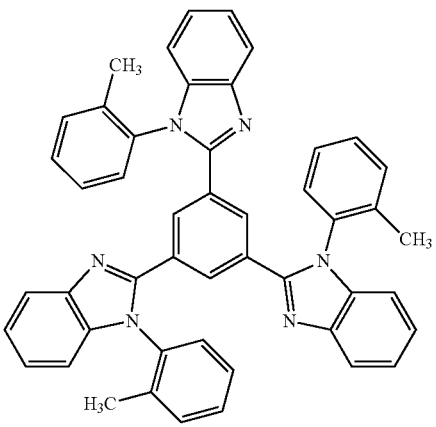

OM-4

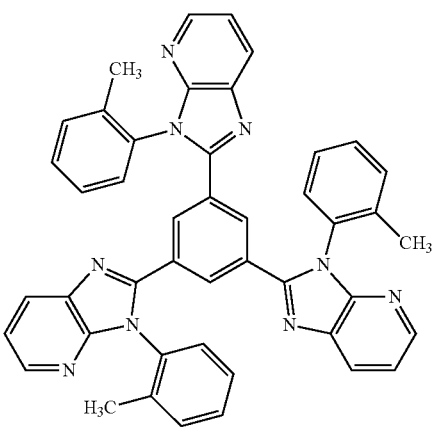

OM-5

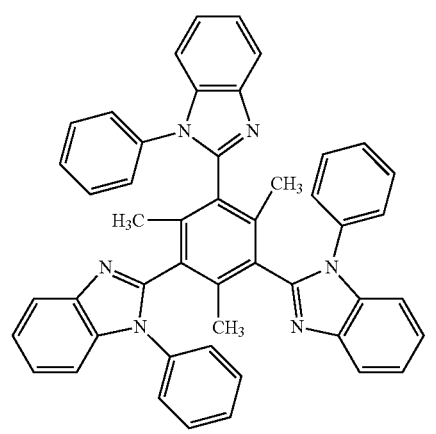

OM-6

OM-7
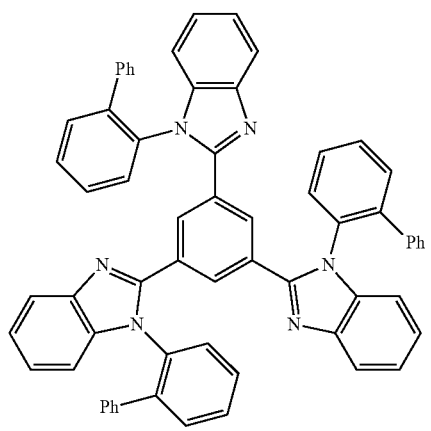
OM-8
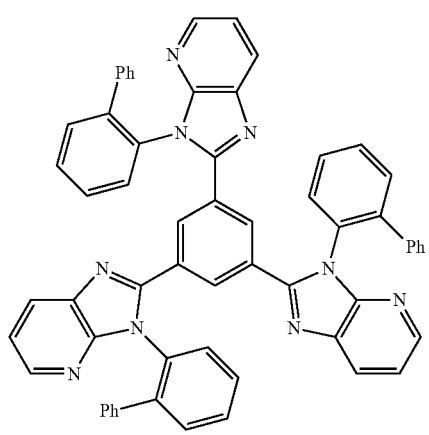
OM-9
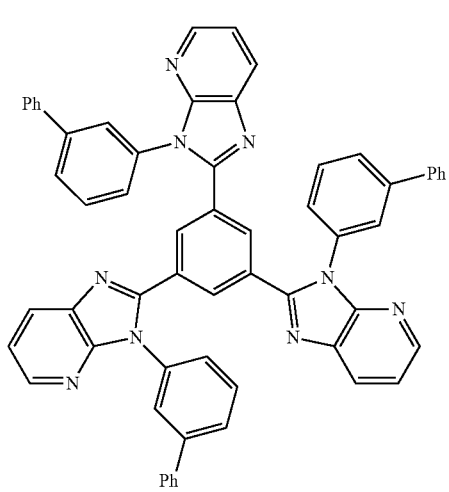
[Chem. 42]
OM-10
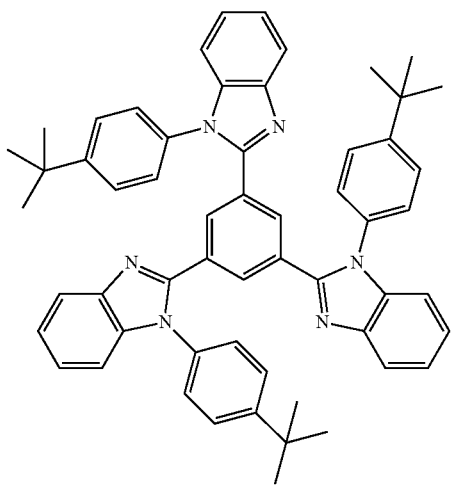
OM-11
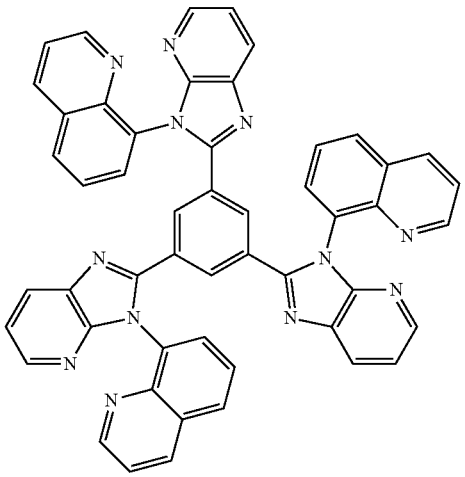
OM-12
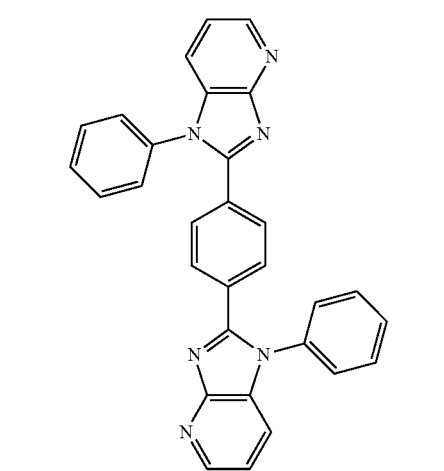

OM-13

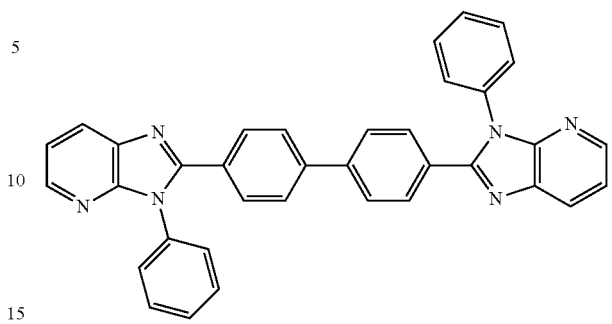

OM-16

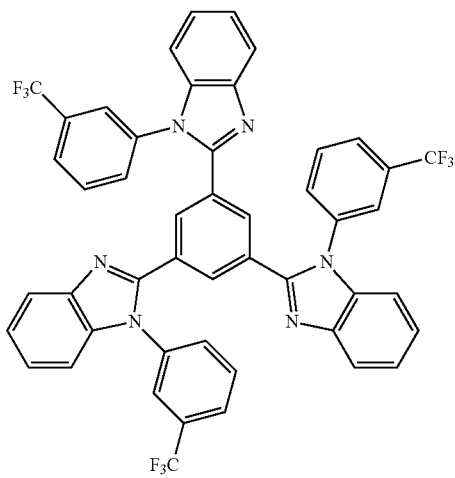

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

OM-14

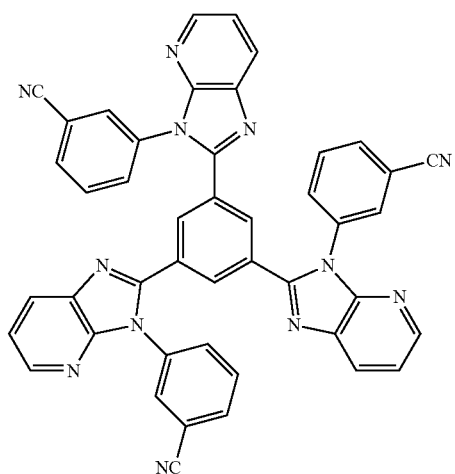

The compound represented by the general formula (O-1) is preferably contained in the amount of 70% by mass to 100% by mass, and more preferably 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

[Chem. 43]

OM-15

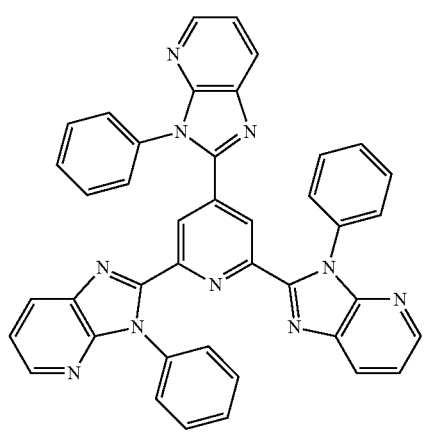

General formula (P)

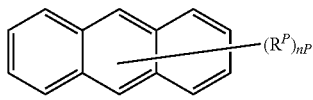

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in the case where there are a plurality of $R^P$'s, these may be the same as or different from each other. At least one of $R^P$'s is a substituent represented by the following general formulae (P-1) to (P-3).

[Chem. 44]

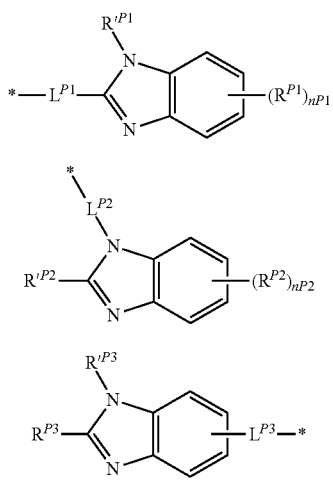

General formula (P-1)

General formula (P-2)

General formula (P-3)

(In the general formulae (P-1) to (P-3), $R^{P1}$ to $R^{P3}$ and $R^{\prime P1}$ to $R^{\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in the case where there are a plurality of $R^{P1}$ to $R^{P3}$ and $R^{\prime P1}$ to $R^{\prime P3}$, these may be the same as or different from each other. $L^{P1}$ to $L^{P3}$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R^{\prime P1}$ to $R^{\prime P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 45]

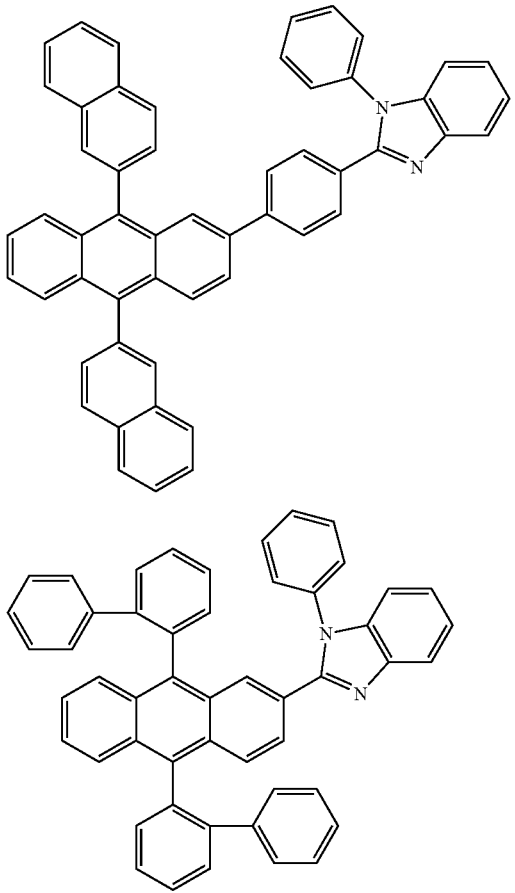

-continued
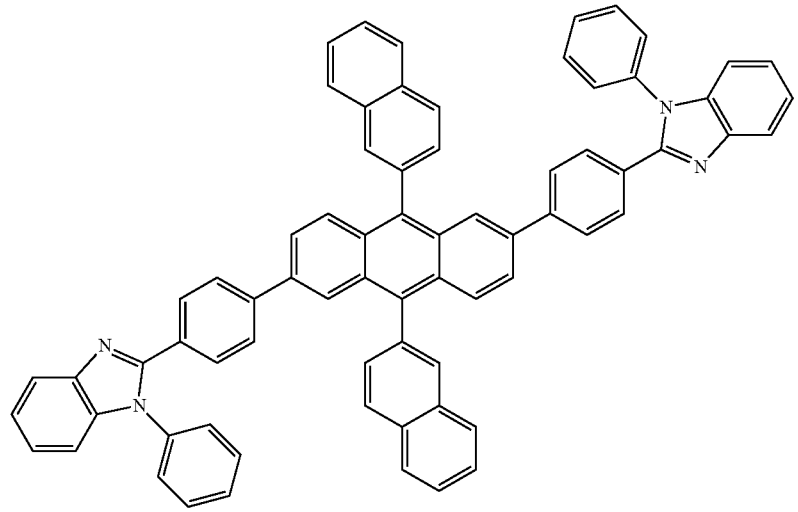
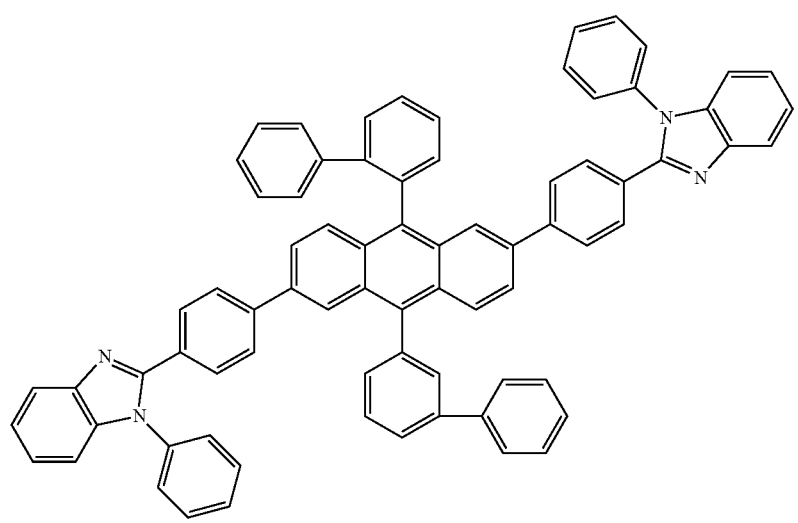
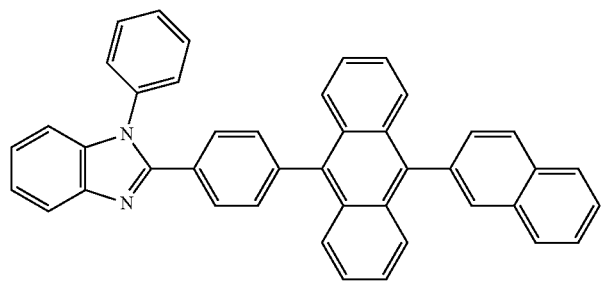
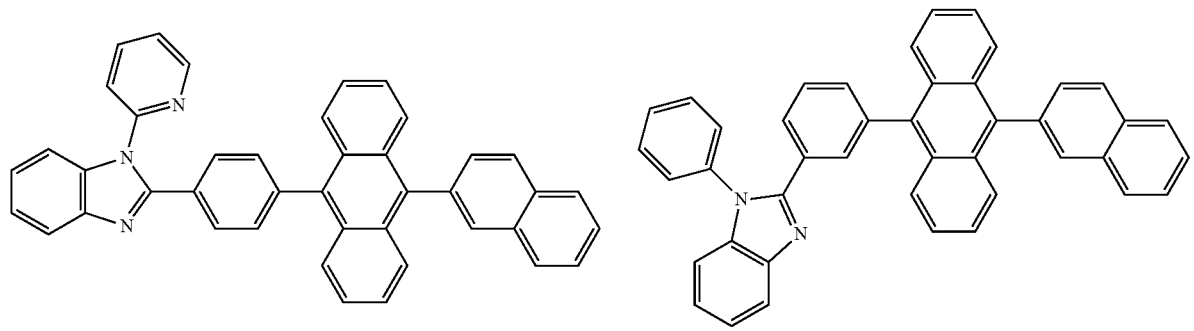

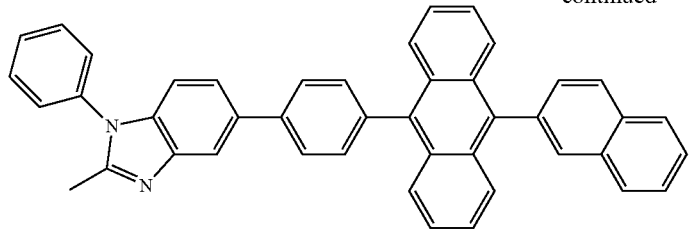

[Chem. 46]

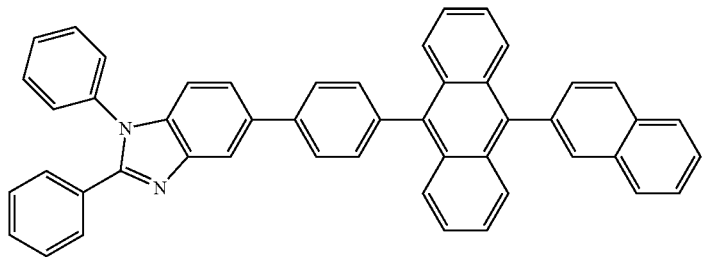

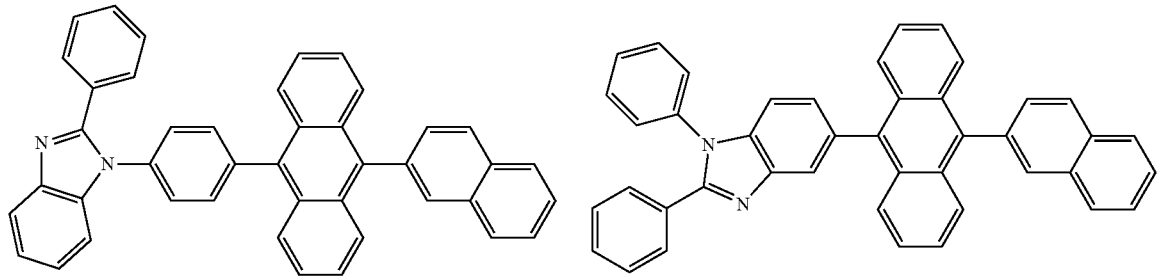

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70% by mass to 100% by mass, and more preferably 85% by mass to 100% by mass, based on the total mass of the organic layer added.

<Protective Layer>

In the present invention, the entirety of the organic electroluminescent element may be protected by a protective layer.

For the protective layer, the detailed description in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of from 300 cd/m$^2$ to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is the same as the maximum light emitting wavelength of the material for the organic electroluminescent element of the present invention, and the element is used for blue light emission among the three primary colors of light. In the organic electroluminescent element of the present invention, the compound represented by the general formula (I) is subjected to blue light emission as the light emitting material.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
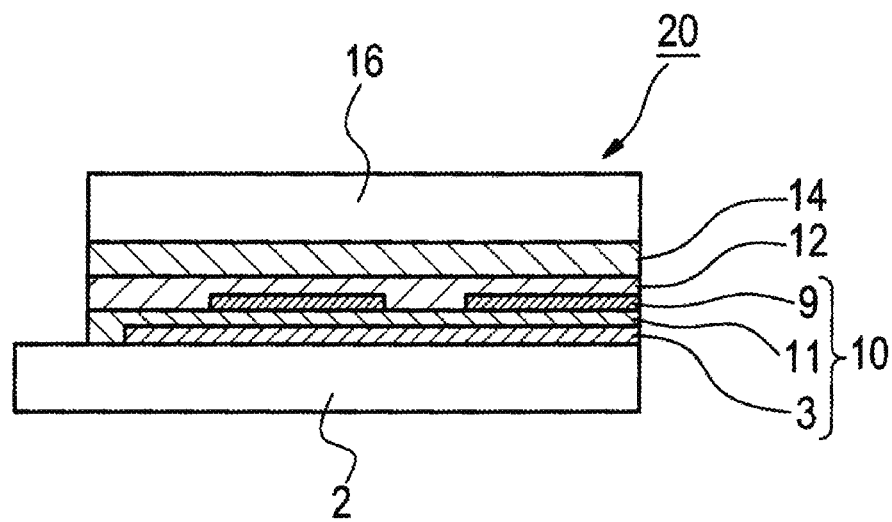
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
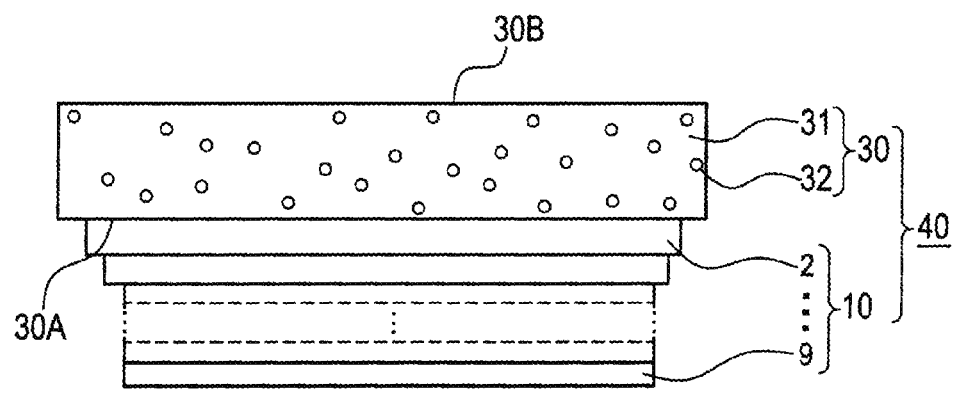
FIG. 3 is a schematic view showing one example of an illumination device according to the present invention.
Figure 4:
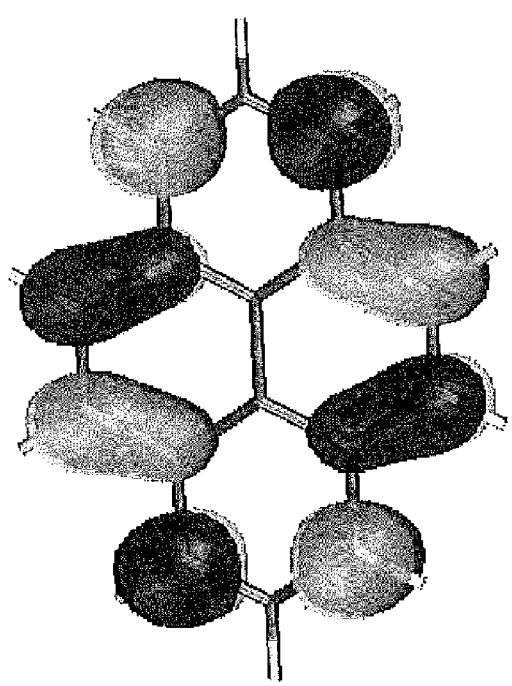
FIG. 4 is a schematic view showing a calculated structure of the arrangement of each orbital with respect to (A) LUMO and (B) HOMO of unsubstituted pyrene.
Figure 4:
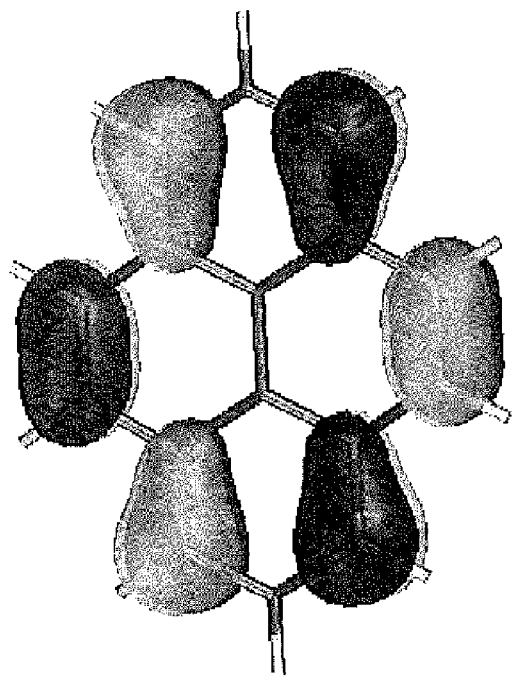

FIG. 3 is a cross-sectional view schematically showing one example of the illumination device of the present invention. The illumination device 40 of the present invention includes, as shown in FIG. 3, the above-described organic EL element 10 and a light scattering member 30.

More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

The structural formulae of the light emitting materials 1 to 5 which are the compounds represented by the general formula (I) used in Examples, and the structural formulae of the light emitting materials Ref-1 to Ref-3 used in Comparative Examples are summarized below. Ref-3 is the compound 88 in PTL 1 (WO2010-012328).

[Chem. 47]

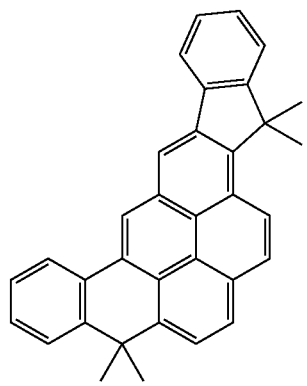

1

2
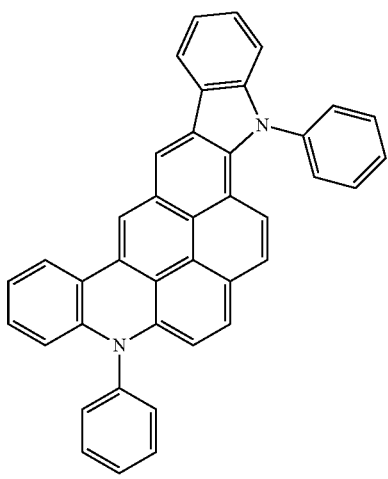

3
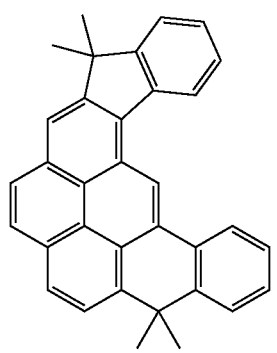

4
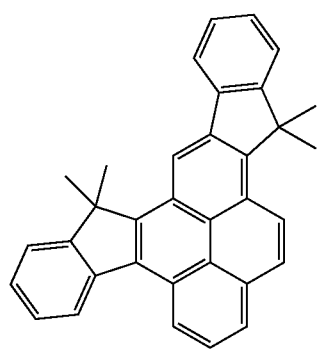

5
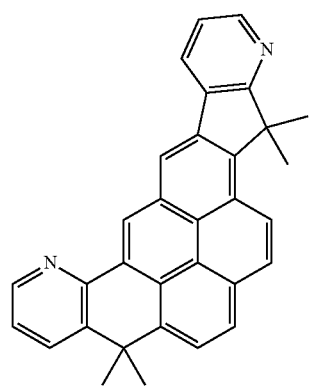

ref-1
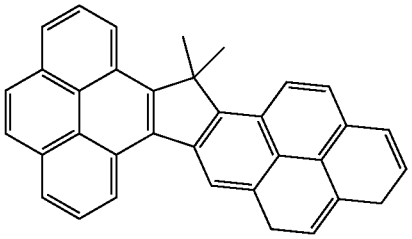

ref-2
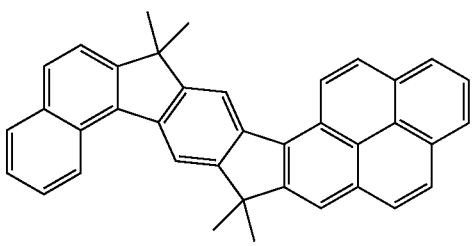

ref-3
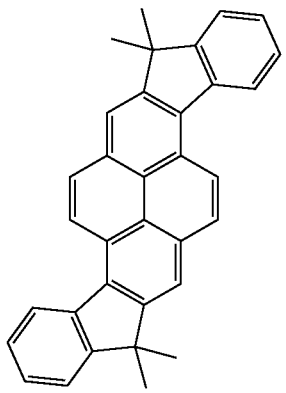

Fabrication and Evaluation of Organic Electroluminescent Element

<Confirmation of Purity>

All of the materials used in the fabrication of the organic electroluminescent element were subjected to sublimation purification, and it was confirmed that the purity (absorption intensity area ratio at 254 nm) was 99.9% or more by using a high performance liquid chromatograph (TSKgel ODS-100Z, manufactured by Tosoh Corporation).

Example 1

Fabrication and Evaluation of by Decomposition of Organic Electroluminescent Element A 0.5 mm-thick and 2.5 cm square glass substrate (manufactured by Geomatec Co., Ltd., surface resistance: 10 Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method.

First layer: HAT-CN: Film thickness 10 nm
Second layer: NPD: Film thickness 30 nm
Third layer: ADN and the light emitting material described in Table 1 (mass ratio=93:7): Film thickness 30 nm Fourth layer: BAlq: Film thickness 30 nm
HAT-CN represents the following structure.

[Chem. 48]

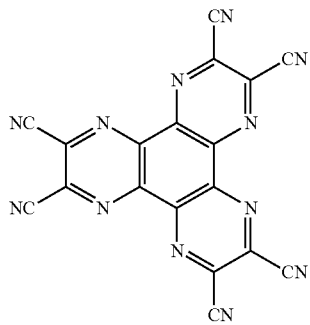

NPD represents the following structure.

[Chem. 49]

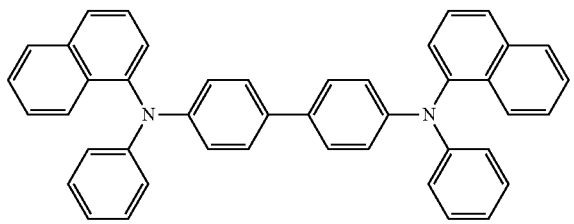

ADN represents the following structure.

[Chem. 50]

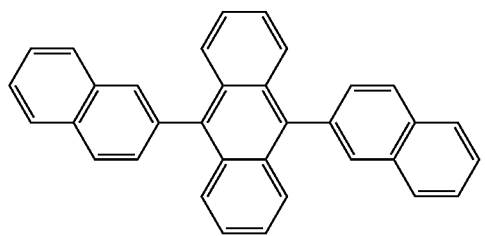

BAlq represents the following structure.

[Chem. 51]

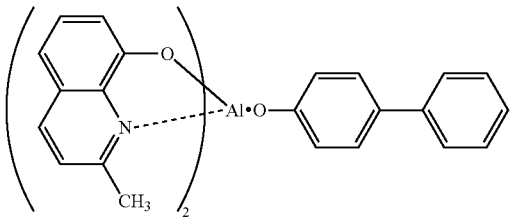

1 nm of lithium fluoride and 100 nm of metallic aluminum were deposited in this order thereon, thereby forming a cathode. At that time, a patterned mask (mask having a light emitting area of 2 mm×2 mm) was placed on the layer of lithium fluoride, and the metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba Ltd.), thereby obtaining organic electroluminescent elements. As a result of light emission with such an element, for any of the elements, light emission derived from the light emitting material was obtained.

<Evaluation of Element> a) Chromaticity

The chromaticity (x, y) was determined from the luminous spectrum when light was emitted by applying a direct current voltage to each of the organic electroluminescent elements to a luminance of 1000 cd/m$^2$ (CIE1931 color system). By the measured y values, the chromaticity of each of the organic electroluminescent elements was evaluated according to the following criteria. The results are shown in Table 1 below.

A: 0.05 or more and less than 0.08
B: 0.08 or more and less than 0.1
C: 0.1 or more and less than 0.15
D: 0.15 or more b) Voltage Each of the driving voltages V1 and V2 was measured when light was emitted by applying a direct current voltage to each of the organic electroluminescent elements to a luminance of 1000 cd/m$^2$ and a luminance of 5000 cd/m$^2$, respectively. Based on the value of V2/V1, evaluation was carried out according to the following criteria. The results are shown in Table 1 below.

A: Less than 1.5
B: 1.5 or more and less than 1.6
C: 1.6 or more and less than 1.7
D: 1.7 or more

TABLE 1

|  | Chromaticity | Voltage |
| --- | --- | --- |
| Organic electroluminescent element 1 of the present invention | B | A |
| Organic electroluminescent element 2 of the present invention | A | B |
| Organic electroluminescent element 3 of the present invention | B | B |
| Organic electroluminescent element 4 of the present invention | B | C |
| Organic electroluminescent element 5 of the present invention | C | A |
| Comparative element 1 | D | C |
| Comparative element 2 | D | D |
| Comparative element 3 | C | D |

From Table 1 above, it was confirmed that the organic electroluminescent element of the present invention emits dark blue light and has a high effect of inhibition of voltage during high-luminance driving.

Example 2

Preparation of Light Emitting Layer-Forming Coating Liquids

The light emitting material 1 (0.25% by mass), ADN represented by the structural formula (5% by mass) as a host material, and toluene (94.75% by mass) were mixed to obtain a light emitting layer-forming coating liquid 1.

Light emitting layer-forming coating liquids 2 and 3 were prepared in the same manner as for the light emitting layer-forming coating liquid 1, except that the light emitting material 1 was changed to light emitting materials 2 and 3 in the light emitting layer-forming coating liquid 1.

Fabrication of Organic Electroluminescent Element

ITO was deposited on a 25 mm×25 mm×0.7 mm glass substrate to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the Electronics Industry (manufactured by Kanto Chemical Co., Inc.) and spin-coated (2,000 rpm, 20 seconds) to give a thickness of about 40 nm, and then dried at 120° C. for 30 minutes and subjected to an annealing treatment at 160° C. for 10 minutes to form a hole injecting layer.

PTPDES-2 represents the following structure.

[Chem. 52]

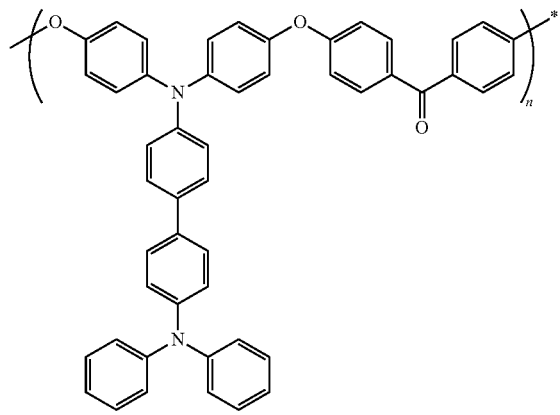

The light emitting layer-forming coating liquids 1 and 3 were spin-coated on the hole injecting layers (1,300 rpm, seconds) to give a thickness of about 40 nm, thereby obtaining light emitting layers.

Subsequently, BAlq represented by the following structural formula was formed as an electron transporting layer on a light emitting layer to give a thickness of 40 nm by a vacuum deposition method.

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a globe box purged with an argon gas, and then sealed with a sealing can made of stainless steel and an ultraviolet ray-curable adhesive (XNR5516HV, manufactured by Nagase-Chiba, Ltd.) to fabricate organic electroluminescent elements 2-1 to 2-3.

It was confirmed that good dark blue light emission was attained from the obtained organic electroluminescent elements 2-1 to 2-3.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

The invention claimed is:

1. An organic electroluminescent element comprising:
a substrate;
a pair of electrodes including an anode and a cathode, disposed on the substrate; and
at least one organic layer including a light emitting layer, disposed between the electrodes,
wherein at least one kind of compound represented by the following general formula (I) is contained in any layer of the at least one organic layer:

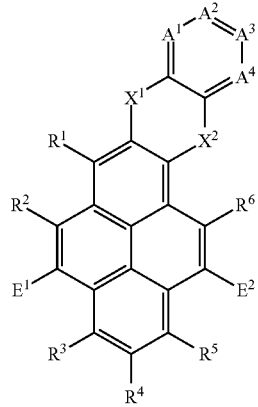

wherein $R^1$ to $R^6$ each independently represent a hydrogen atom or a substituent, but there is no case where two adjacent groups out of $R^1$ to $R^6$ are bonded to each other to form a ring; $E^1$ and $E^2$ each independently represents a hydrogen atom or a substituent; one of the set of $E^1$ and $R^2$, $E^1$ and $R^3$, $E^2$ and $R^6$, and $E^2$ and $R^5$ is bonded to each other to form a structure represented by the following general formula (E-1), and the remaining members of the set are not bonded to each other to form a ring:

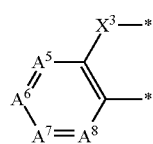

\* represents a position for bonding to the pyrene skeleton; of $X^1$ and $X^2$, one represents a single bond and the other represents any linking group selected from $CR^{111}R^{112}$, $NR^{113}$, O, S, and $SiR^{114}R^{115}$; $X^3$ represents any linking group selected from $CR^{111}R^{112}$, $NR^{113}$, O, S, and $SiR^{114}R^{115}$; $R^{111}$ to $R^{115}$ each independently represent a hydrogen atom or a substituent; $A^1$ to $A^8$ each independently represents $CR^{116}$ or N; $R^{116}$ represents a hydrogen atom or a substituent, and when two adjacent groups out of $A^1$ to $A^4$ are $CR^{116}$, the two $R^{116}$'s may be bonded to each other to form a ring structure.

2. The organic electroluminescent element according to claim 1, wherein the compound represented by the general formula (I) is a compound represented by the following general formula (II):

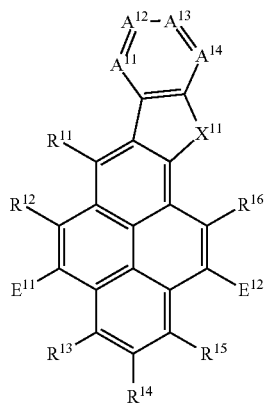

wherein $R^{11}$ to $R^{16}$ each independently represent a hydrogen atom or a substituent, but there is no case where two adjacent groups out of $R^{11}$ to $R^{16}$ are bonded to each other to form a ring; $E^{11}$ and $E^{12}$ each independently represent a hydrogen atom or a substituent; one of the set of $E^{11}$ and $R^{12}$, $E^{11}$ and $R^{13}$, $E^{12}$ and $R^{16}$, and $E^{12}$ and $R^{15}$ is bonded to each other to form a structure represented by the following general formula (E-1), and the remaining members of the set are not bonded to each other to form a ring:

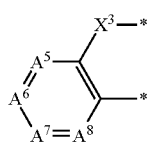

\* represents a position for bonding to the pyrene skeleton; $X^{11}$ and $X^2$ each independently represents any linking group selected from $CR^{111}R^{112}$, $NR^{113}$, O, S, and $SiR^{114}R^{115}$; $X^3$ represents any linking group selected from $CR^{111}R^{112}$, $NR^{113}$, O, S, and $SiR^{114}R^{115}$; $R^{111}$ to $R^{115}$ each independently represents a hydrogen atom or a substituent; $A^{11}$ to $A^{14}$ and $A^5$ to $A^8$ each independently represents $CR^{116}$ or N; $R^{116}$ represents a hydrogen atom or a substituent, and when two adjacent groups out of $A^{11}$ to $A^{14}$ and $A^5$ to $A^8$ are $CR^{116}$, the two $R^{116}$'s may be bonded to each other to form a ring structure.

3. The organic electroluminescent element according to claim 1, wherein the compound represented by the general formula (I) is a compound represented by the following general formula (III):

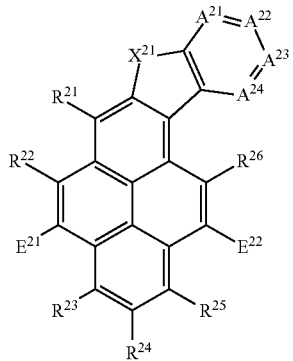

wherein $R^{21}$ to $R^{26}$ each independently represent a hydrogen atom or a substituent, but there is no case where two adjacent groups out of $R^{21}$ to $R^{26}$ are bonded to each other to form a ring; $E^{21}$ and $E^{22}$ each independently represent a hydrogen atom or a substituent; one of the set of $E^{21}$ and $R^{22}$, $E^{21}$ and $R^{23}$, $E^{22}$ and $R^{26}$, and $E^{22}$ and $R^{25}$ is bonded to each other to form a structure represented by the following general formula (E-1) and the remaining members of the set are not bonded to each other to form a ring:

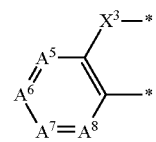

\* represents a position for bonding to the pyrene skeleton; $X^{21}$ and $X^2$ each independently represent any linking group selected from $CR^{111}R^{112}$, $NR^{113}$, O, S, and $SiR^{114}R^{115}$; $X^3$ represents any linking group selected from $CR^{111}R^{112}$, $NR^{113}$, O, S, and $SiR^{114}R^{115}$; $R^{111}$ to $R^{115}$ each independently represent a hydrogen atom or a substituent; $A^{21}$ to $A^{24}$ and $A^5$ to $A^8$ each independently represents $CR^{116}$ or N; $R^{116}$ represents a hydrogen atom or a substituent, and when two adjacent groups out of $A^{21}$ to $A^{24}$ and $A^5$ to $A^8$ are $CR^{116}$, the two $R^{116}$'s may be bonded to each other to form a ring structure.

4. The organic electroluminescent element according to claim 2, wherein the compound represented by the general formula (II) is a compound represented by any one of the following general formulae (IV) to (VII);

General formula (IV)

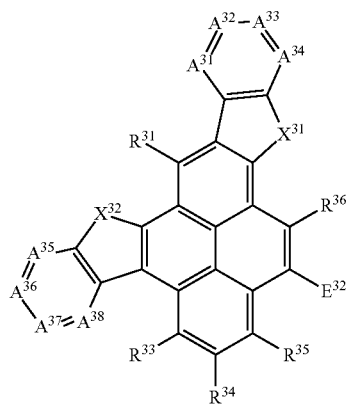

General formula (V)

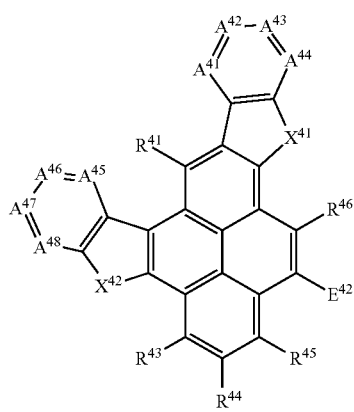

General formula (VI)

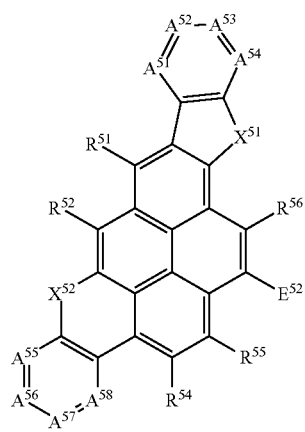

General formula (VII)

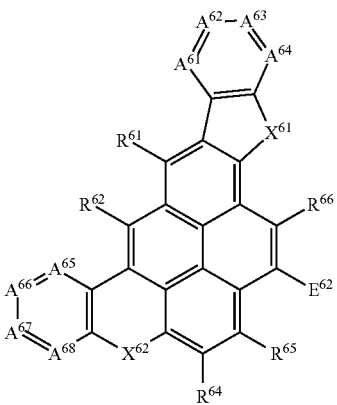

wherein $R^{31}$ to $R^{66}$ and $E^{32}$ to $E^{62}$ each independently represents a hydrogen atom or a substituent, but there is no case where two adjacent groups out of $R^{31}$ to $R^{66}$ and $E^{32}$ to $E^{62}$ are bonded to each other to form a ring; $X^{32}$ to $X^{62}$ represent any linking group selected from $CR^{111}R^{112}$, $NR^{113}$, O, S, and $SiR^{114}R^{115}$; $R^{111}$ to $R^{115}$ each independently represent a hydrogen atom or a substituent;

$A^{31}$ to $A^{68}$ each independently represent $CR^{116}$ or N; $R^{116}$ represents a hydrogen atom or a substituent, and when two adjacent groups out of $A^{31}$ to $A^{68}$ are $CR^{116}$, the two $R^{116}$'s may be bonded to each other to form a ring structure.

5. The organic electroluminescent element according to claim 2, wherein the compound represented by the general formula (II) is a compound represented by any one of the following general formulae (VIII) to (XI);

General formula (VIII)

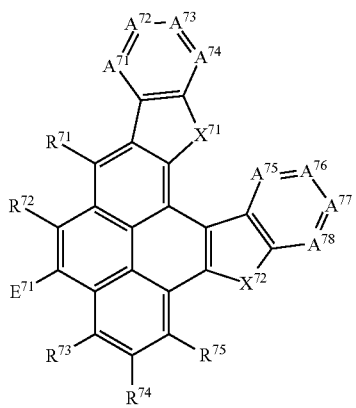

-continued

General formula (IX)

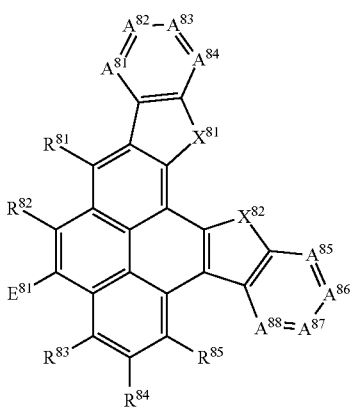

General formula (X)

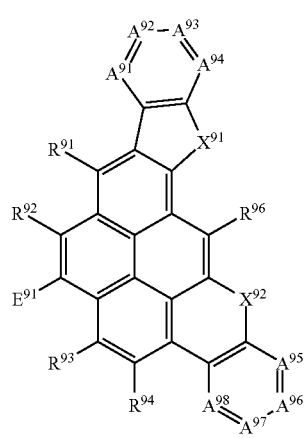

General formula (XI)

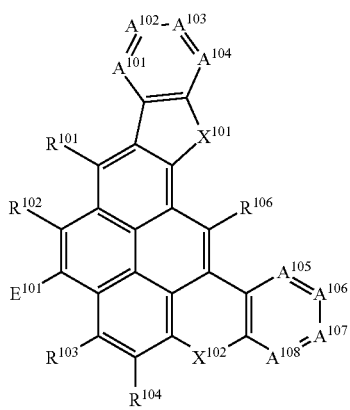

wherein $R^{71}$ to $R^{106}$ and $E^{72}$ to $E^{102}$ each independently represent a hydrogen atom or a substituent, but there is no case where two adjacent groups out of $R^{71}$ to $R^{106}$ and $E^{72}$ to $E^{102}$ are bonded to each other to form a ring; $X^{72}$ to $X^{102}$ represent any linking group of $CR^{111}R^{112}$, $NR^{113}$, O, S, and $SiR^{114}R^{115}$; $R^{111}$ to $R^{115}$ each independently represent a hydrogen atom or a substituent; $A^{71}$ to $A^{108}$ each independently represent $CR^{116}$ or N; $R^{116}$ represents a hydrogen atom or a substituent, and when two adjacent groups out of $A^{71}$ to $A^{108}$ are $CR^{116}$, the two $R^{116}$'s may be bonded to each other to form a ring structure.

6. The organic electroluminescent element according to claim 1, wherein the molecular weight of the compound represented by the general formula (I) is 800 or less.

7. The organic electroluminescent element according to claim 1, wherein the compound represented by the general formula (I) is contained in the light emitting layer.

8. The organic electroluminescent element according to claim 7, wherein the compound represented by the general formula (I) is a light emitting material contained in the light emitting layer.

9. The organic electroluminescent element according to claim 8, further comprising a host material in the light emitting layer.

10. The organic electroluminescent element according to claim 9, wherein the host material has a hydrocarbon fused ring structure having 10 to 50 carbon atoms.

11. The organic electroluminescent element according to claim 9, wherein the host material has an anthracene skeleton.

12. The organic electroluminescent element according to claim 1, wherein the organic layer containing the compound represented by the general formula (I) is formed by a vacuum deposition process.

13. The organic electroluminescent element according to claim 1, wherein the light emitting layer is formed by a wet process.

14. A light emitting device using the organic electroluminescent element according to claim 1.

15. A display device using the organic electroluminescent element according to claim 1.

16. An illumination device using the organic electroluminescent element according to claim 1.

17. A compound represented by the following general formula (I):

General formula (I)

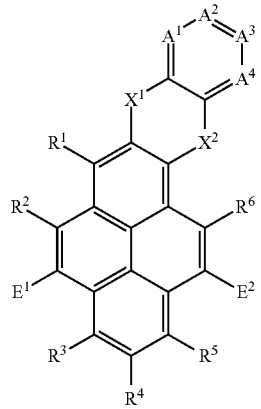

wherein $R^1$ to $R^6$ each independently represent a hydrogen atom or a substituent, but there is no case where two adjacent groups out of $R^1$ to $R^6$ are bonded to each other to form a ring; $E^1$ and $E^2$ each independently represents a hydrogen atom or a substituent; one of the set of $E^1$ and $R^2$, $E^1$ and $R^3$, $E^2$ and $R^6$, and $E^2$ and $R^5$ is bonded to each other to form a structure represented by the following general formula (E-1), and the remaining members of the set are not bonded to each other to form a ring:

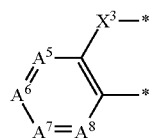

* represents a position for bonding to the pyrene skeleton; of $X^1$ and $X^2$, one represents a single bond and the other represents any linking group selected from $CR^{111}R^{112}$, $NR^{113}$, O, S, and $SiR^{114}R^{115}$; $X^3$ represents any linking group of $CR^{111}R^{112}$, $NR^{113}$, O, S, and $SiR^{114}R^{115}$; $R^{111}$ to $R^{115}$ each independently represent a hydrogen atom or a substituent; $A^1$ to $A^8$ each independently represent $CR^{116}$ or N; $R^{116}$ represents a hydrogen atom or a substituent, and when two adjacent groups out of $A^1$ to $A^4$ are $CR^{116}$, the two $R^{116}$'s may be bonded to each other to form a ring structure.

* * * * *